US006579682B1

(12) United States Patent
Innerarity et al.

(10) Patent No.: US 6,579,682 B1
(45) Date of Patent: Jun. 17, 2003

(54) METHODS AND TOOLS FOR IDENTIFYING COMPOUNDS WHICH MODULATE ATHEROSCLEROSIS BY IMPACTING LDL-PROTEOGLYCAN BINDING

(75) Inventors: Thomas Innerarity, Lafayette, CA (US); Jan Boren, Gothenburg (SE)

(73) Assignee: The Regents of University of California, Oakland, CA (US)

( * ) Notice: Subject to any disclaimer, the term of this patent is extended or adjusted under 35 U.S.C. 154(b) by 0 days.

(21) Appl. No.: 09/265,222

(22) Filed: Mar. 5, 1999

Related U.S. Application Data

(60) Provisional application No. 60/077,618, filed on Mar. 10, 1998.

(51) Int. Cl.$^7$ ............................................. G01N 33/53

(52) U.S. Cl. ..................... 435/7.1; 435/7.94; 436/518; 436/13; 436/71; 530/359; 530/389.3

(58) Field of Search .................. 435/7.1, 7.5, 7.94; 436/518, 13, 71; 530/359, 389.3

(56) References Cited

U.S. PATENT DOCUMENTS

| 4,683,195 | A | 7/1987 | Mullis et al. |
|---|---|---|---|
| 4,683,202 | A | 7/1987 | Mullis |
| 5,139,941 | A | 8/1992 | Muzyczka et al. |
| 5,350,671 | A | 9/1994 | Houghton et al. |
| 5,399,346 | A | 3/1995 | Anderson et al. |
| 5,580,859 | A | 12/1996 | Felgner et al. |
| 5,656,465 | A | 8/1997 | Panicali et al. |
| 5,672,344 | A | 9/1997 | Kelley et al. |
| 5,851,529 | A | 12/1998 | Guber et al. |

FOREIGN PATENT DOCUMENTS

| EP | 0 200 362 B1 | 12/1986 |
|---|---|---|
| EP | 0 201 184 B1 | 12/1986 |
| EP | 0 229 701 B1 | 7/1987 |
| WO | WO 84/03506 | 9/1984 |
| WO | WO 84/03564 | 9/1984 |
| WO | WO 95/04064 | 2/1995 |

OTHER PUBLICATIONS

Camejo et al., "Factors modulating the interaction of LDL with an arterial lipoprotein complexing proteoglycan: The effect of HDL" *Acta. Med. Scand. Suppl.* (1980) 642:159–164.
Christner et al., "A competitive assay of lipoprotein:Proteoglycan interaction using a 96–well microtitration plate" *Analytical Biochem.* (1990) 184:388–394.
Eisenberg et al., "Lipoprotein lipase enhances binding of lipoproteins to heparan sulfate on cell surfaces and extracellular matrix" *J. Clin. Invest.* (1992) 90:2013–2021.
Hurt et al., "Interaction of LDL with human arterial proteoglycans stimulates its uptake by human monocyte–derived macrophages" *J. Lipid Res.* (1990) 31:443–454.
Pentikäinen et al., "The proteoglycan decorin links low density lipoproteins with collagen Type I" *J. Biolog. Chem.* (1997) 272:7633–7638.
van Barlingen et al., "Lipoprotein lipase–enhanced binding of human triglyceride–rich lipoproteins to heparan sulfate: modulation by apolipoprotein E and apolipoprotein C" *Journal of Lipid Res.* (1996) 37:754–763.
*Antibodies: A Laboratory Manual,* (1988) Ed Harlow, David Lane, eds., (Table of Contents).
Arnold et al., Lipoprotein–receptor interactions (1992) *Lipoprotein Analysis. A Practical Approach,* C. A. Converse and E. R. Skinner, eds., Oxford University Press, Oxford, pp. 145–168.
Basu et al., "Degradation of cationized low density lipoprotein and regulation of cholesterol metabolism in homozygous familial hypercholesterolemia fibroblasts" (1976) *Proc. Natl. Acad. Sci.* USA 73:3178–3182.
Borén et al., "A simple and efficient method for making site–directed mutants, deletions, and fusions of large DNA such as P1 and BAC clones" (1996) *Genome Res.* 6:1123–1130.
Borén et al., "Identification of the low density lipoprotein receptor–binding site in apolipoprotein B100 and the modulation of its binding activity by the carboxyl terminus in familial defective apo–B100" (1998) *J. Clin. Invest.* 101:1084–1093.
Camejo et al., "Identification of Apo B–100 segments mediating the interaction of low density lipoproteins with arterial proteoglycans" (1988) *Arteriosclerosis* 8:368–377.
Camejo et al., "Binding of low density lipoproteins by proteoglycans synthesized by proliferating and quiescent human arterial smooth muscle cells" (1993) *J. Biol. Chem.* 268:14131–14137.
Capecchi, Mario R., "Altering the genome by homologous recombination" (1989) *Science* 244:1288–1292.
Cardin et al., "Physical–chemical interaction of heparin and human plasma low–density lipoproteins" (1987) *Biochemistry* 26:5513–5518.
Cardoso et al., "Glycosaminoglycan fractions from human arteries presenting diverse susceptibilities to atherosclerosis have different binding affinities to plasma LDL" (1994) *Arterioscler. Thromb.* 14:115–124.

(List continued on next page.)

Primary Examiner—Long V. Le
(74) Attorney, Agent, or Firm—Morrison & Foerster LLP

(57) ABSTRACT

The present invention relates to the study and control of atherosclerosis through the modulation of LDL-proteoglycan binding at Site B (amino acids 3359–3369) of the apo-B100 protein in LDL. The invention encompasses methods of identifying compounds which modulate LDL-proteoglycan binding, methods of identifying compounds which modulate atherosclerotic lesion formation, and methods of modulating the formation of atherosclerotic lesions. The invention also encompasses mutant apo-B100 proteins and LDL which exhibit reduced proteoglycan binding while maintaining LDL-receptor binding, polynucleotides which encode these apo-B100 proteins, as well as cells and animals which express the mutant apo-B100 proteins.

5 Claims, 6 Drawing Sheets

OTHER PUBLICATIONS

Chang et al., "Proteoglycans synthesized by smooth muscle cells derived from monkey (*Macaca nemestrina*) aorta" (1983) *J. Biol. Chem.* 258:5679–5688.

Corsini et al., "Receptor binding activity of lipid recombinants of apolipoprotein B–100 thrombolytic fragments" (1987) *J. Lipid Res.* 28:1410–1423.

Costa et al., "Polishing with T4 or Pfu polymerase increases the efficiency of cloning of PCR fragments" (1994) *Nucleic Acids Res.* 22:2423.

Deng et al., "Site–directed mutagenesis of virtually any plasmid by eliminating a unique site" (1992) *Anal. Biochem.* 200:81–88.

Edwards et al., "Lipoprotein lipase enhances the interaction of low density lipoproteins with artery–derived extracellular matrix proteoglycans" (1993) *J. Lipid Res.* 34:1155–1163.

Gaffney et al., "Independent mutations at codon 3500 of the apoliprotein B gene are associated with hyperlipidemia" (1995) *Arterioscler. Thromb. Vasc. Biol.* 15:1025–1029.

Galis et al., "Co–localization of aortic apoliprotein B and chondroitin sulfate in an injury model of atherosclerosis" (1993) *Am J. Pathol.* 142:1432–1438.

Geysen et al., "Use of peptide synthesis to probe viral antigens for epitopes to a resolution of a single amino acid" (1984) *Proc. Natl. Acad. Sci. USA* 81:3998–4002.

Goldstein et al., "Receptor–mediated endocytosis: Concepts emerging from the LDL receptor system" (1985) *Annu. Rev. Cell Biol.* 1:1–39.

Hirose et al., "Isolation and characterization of four heparin–binding cyanogen bromide peptides of human plasma apolipoprotein B" (1987) *Biochemistry* 26:5505–5512.

Hobbs et al., "Molecular genetics of the LDL receptor gene in familial hypercholesterolemia" (1992) *Hum. Mutat.* 1:445–466.

Hoff et al., "Plasma low density lipoprotein accumulationin aortas of hypercholesterolemic swine correlates with modifications in aortic glycosaminoglycan composition" (1986) *Atherosclerosis*. 61:231–236.

Hoff et al., "Apolipoprotein B localization in coronary atherosclerotic plaques from cynomolgus monkeys" (1983) *Artery* 12:104–116.

Hu, Gengxi, "DNA polymerase–catalyzed addition of non-templated extra nucleotides to the 3'end of a DNA fragment" (1993) *DNA and Cell Biology* 12:763–770.

Hurt et al., "Effect of arterial proteoglycans on the interaction of LDL with human monocyte–derived macrophages" (1987) *Atherosclerosis* 67:115–126.

Hurt–Camejo et al., "Cellular consequences of the association of apoB lipoproteins with proteoglycans" (1997) *Arterioscler Thromb Vasc Biol.* 17:1011–1017.

Innerarity et al., "Familial defective apolipoprotein B–100: Low density lipoproteins with abnormal receptor binding" (1987) *Proc. Natl. Acad. Sci. USA* 84:6919–6923.

Innerarity et al., "Familial defective apolipoprotein B–100: a mutation of apolipoprotein B that causes hypercholestrolemia" (1990) *J. Lipid Res.* 31:1337–1349.

Ismail et al., "Lipoprotein–proteoglycan complexes from injured rabbit arotas accelerate lipoprotein uptake by arterial smooth muscle cells" (1994) *Atherosclerosis* 105:79–87.

Johnstone et al., "Purification of immunoglobulins" (1996) *Immunochemistry in Practice,* Blackwell Scientific Publications, Oxford, p. 69.

Knott et al, "Human apolipoprotein B: Structure of carboxyl–terminal domains, sites of gene expression, and chromosomal localization" (1985) *Science.* 230:37–43.

Knott et al., "Complete protein sequence and identification of structural domains of human apolipoprotein B" (1986) *Nature* 323:734–738.

Kunkel, Thomas A., "Rapid and efficient site–specific mutagenesis without phenotypic selection" (1985) *Proc. Natl. Acad. Sci. U.S.A.* 82:488–492.

Lindén et al., "Affinity of LDL to a human arterial proteoglycan among male survivors of myocardial infarction" (1989) *Eur. J. Clin. Invest.* 19:38–44.

Linton et al., "Transgenic mice expressing high plasma concentrations of human apolipoprotein B100 and lipoprotein (a)" (1993) *J. Clin. Invest.* 92:3029–3037.

Mahley et al., "Inhibition of lipoprotein binding to cell surface receptors of fibroblasts following selective modification of arginyl residues in arginine–rich and B apoproteins" (1977) *J. Biol Chem* 252:7279–7287.

Mahley et al., "Interaction of plasma lipoproteins containing apolipoproteins B and E with heparin and cell surface receptors" (1979) *Biochem. Biophys. Acta.* 575:81–91.

McCormick et al., "Expression of P1 DNA in mammalian cells and transgenic mice" (1994) *Genet. Anal. Tech. Appl.* 11:158–164.

Merrilees et al., "Glycosaminoglycan synthesis by smooth muscle cells of differing phenotype and their response to endothelial cell conditioned medium" (1990) *Arteriosclerosis* 81:245–254.

*Methods in Enzymology* (1979) Sidney P. Colowick and Nathan O. Kaplan, eds., Academic Press, Inc. (Table of Contents).

Milne et al., "Characterization of monoclonal antibodies against human low density lipoprotein" (1983) *Arteriosclerosis* 3:23–30.

*Molecular Cloning: A Laboratory Manual,* Second Edition, (1989) J. Sambrook et al., eds., Cold Spring Harbor Laboratory Press (Table of Contents).

Mullis et al., "Specific synthesis of DNA in vitro via a polymerase–catalyzed chain reaction" *Methods in Enzymology* (1987) 155:335–350.

Nelson et al., "Use of DNA methyltransferase/endonuclease enzyme combinations for megabase mapping of chromosomes" (1992) *Methods Enzymol.* 216:279–303.

Nievelstein–Post et al., "An ultrastructural study of lipoprotein accumulation in cardiac valves of the rabbit" (1994) *Arterioscler. Thromb.* 14:1151–1161.

*Nucleic Acid Hybridisation. A Practical Approach* (1985) B. D. Hames & S. J. Higgins, eds., IRL Press. (Table of Contents).

*Oligonucleotide Synthesis. A Practical Approach* (1984) M.J. Gait, ed., IRL Press, (Table of Contents).

Olsson et al., "Possible functional interactions of apolipoprotein B–100 segments that associate with cell proteoglycans and the ApoB/E receptor" (1997) *Arterioscler. Throm. Vasc. Biol.* 17:149–155.

Paananen et al., "Proteolysis and fusion of low density lipoprotein particles independently strenghen their binding to exocytosed mast cell granules" (1994) *J. Biol. Chem.* 269:2023–2031.

*PCR Technology* (1989) H.A. Erlich ed., Stockton Press, (Table of Contents).

*Protein Purification: Principles and Practice, Second Edition,* Scopes, Robert K., (1987) Springer–Verlag, (Table of Contents).

Pullinger et al., "Familial ligand–defective apolipoprotein B" (1995) *J. Clin. Invest.* 95:1225–1234.

Radhakrishnamurthy et al., "Arterial wall proteoglycans— biolgical properties related to pathogenesis of atherosclerosis" (1990) *Eur. Heart J.* 11 (Suppl E): 148–157.

Ross, Russell, "Cell biology of atherosclerosis" (1995) *Annu. Rev. Physiol.* 57:791–804.

Saiki et al., "Primer–directed enzymatic amplification of DNA with a thermostable DNA polymerase" (1988) *Science* 239:487–491.

Schönherr et al., "Effects of platelet–derived growth factor and transforming growth factor–$\beta$1 on the synthesis of a large versican–like chondroitin sulfate proteoglycan by arterial smooth muscle cells" (1991) *J. Biol. Chem.* 266:17640–17647.

Schönherr et al., "Platelet–derived growth factor and transforming growth factor–$\beta$1 differentially affect the synthesis of biglycan and decorin by monkey arterial smooth muscle cells" (1993) *Arterioscler. Thromb.* 13:1026–1036.

Steele et al., "Artery wall derived proteoglycan–plasma lipoprotein interaction: lipoprotein binding properties of extracted proteoglycans" (1987) *Atherosclerosis* 65:51–62.

Vandeyar et al., "A simple and rapid method for the selection of oligodeoxynucleotide–directed mutants" (1988) *Gene* 65:129–133.

Walton et al., "Histological and immunolfuorescent studies on the evolution of the human atheromatous plaque" (1968) *J. Atheroscler. Res.* 8:599–624.

Weiner et al., "Site–directed mutagenesis of double–stranded DNA by the polymerase chain reaction" (1994) *Gene* 151:119–123.

Weisgraber et al., "Role of the lysine residues of plasma lipoproteins in high affinity binding to cell surface receptors on human fibroblasts" (1978) *J. Biol. Chem.* 253:9053–9062.

Weisgraber et al., "Human apolipoprotein E: Determination of the heparin binding sites of apolipoprotein E3" (1986) *J. Biol. Chem.* 261:2068–2076.

Weisgraber et al., "Human apolipoprotein B–100 heparin-binding sites" (1987) *J. Biol. Chem.* 262:11097–11103.

Williams et al., "The response–to–retention hypothesis of early atherogenesis" (1995) *Arterioscier. Thromb. Vasc Biol.* 15:551–561.

Yao et al., "Elimination of apolipoprotein B48 formation in rat hepatoma cell lines transfected with mutant human apolipoprotein B cDNA constructs" (1992) *J. Biol Chem.* 267:1175–1182.

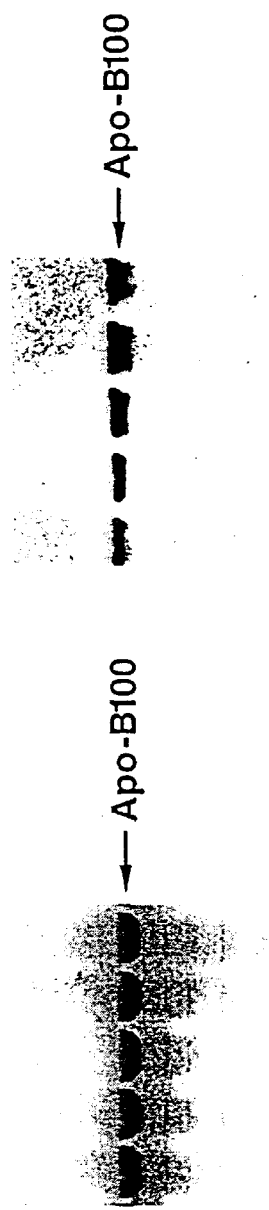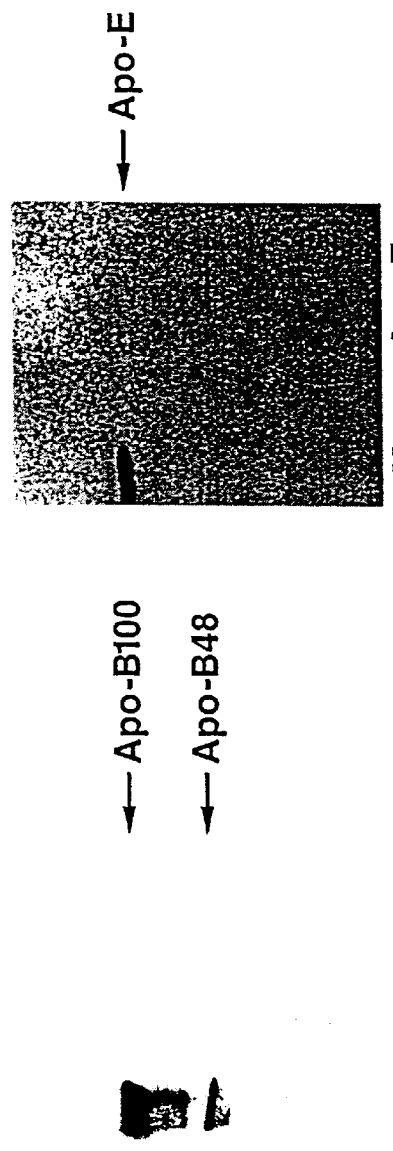
FIG. 1A Coomassie Stain
FIG. 1B Human Apo-B
FIG. 1C Mouse Apo-B
FIG. 1D Mouse Apo-E

METHODS AND TOOLS FOR IDENTIFYING COMPOUNDS WHICH MODULATE ATHEROSCLEROSIS BY IMPACTING LDL-PROTEOGLYCAN BINDING

This application claims priority under 35 USC §119(e) to U.S. Provisional Application Serial No. 60/077,618, filed Mar. 10, 1998, the entire contents of which are incorporated herein by reference.

STATEMENT OF RIGHTS TO INVENTIONS MADE UNDER FEDERALLY SPONSORED RESEARCH

The invention was funded in part by National Institutes of Health program project grant HL41633. The U.S. Government may have certain rights to this invention.

TECHNICAL FIELD

This invention relates to the disease atherosclerosis, methods of modulating the formation of atherosclerotic lesions, and methods of identifying compounds which modulate atherosclerotic lesion formation. Specifically the invention relates to the reduction of atherosclerosis through the modulation of LDL-proteoglycan binding at Site B (amino acids 3359–3369) of the apo-B100 protein in LDL.

BACKGROUND ART

High levels of LDL are a major risk factor for coronary disease and are the source for most of the cholesterol that accumulates in the arterial wall (Ross, R. 1995. *Annu. Rev. Physiol.* 57:791–804). Subendothelial retention of LDL has been suggested to be a key pathogenic process in atherosclerosis, and several lines of circumstantial evidence suggest that intramural retention of atherogenic lipoproteins involves the extracellular matrix, chiefly proteoglycans (Hurt-Camejo, E. et al. 1997. *Arterioscler Thromb Vasc Biol.* 17:1011–1017; Williams, K. J., and I. Tabas. 1995. *Arterioscier. Thromb. Vasc. Biol.* 15:551–561; and Radhakrishnamurthy, B. et al. 1990. *Eur. Heart J.* 11 Suppl E: 148–157).

The significance of the possible LDL proteoglycan interaction has been highlighted in two recent review articles (Hurt-Camejo, E. et al. 1997. *Arterioscler Thromb Vasc Biol.* 17:1011–1017; and Williams, K. J., and I. Tabas. 1995. *Arterioscier. Thromb. Vasc Biol.* 15:551–561). Williams and Tabas proposed that subendothelial retention of atherogenic lipoproteins is the central pathogenic process in atherosclerosis. Moreover, they hypothesized that retained lipoproteins can directly or indirectly provoke all known features of early lesions, such as lipoprotein oxidation, monocyte migration into the artery wall, macrophage foam cell formation, and cytokine production, and can accelerate further retention by stimulating local synthesis of proteoglycans. Several lines of evidence indicate that the retention of arterial lipoproteins involves the extracellular matrix; proteoglycans in particular have been hypothesized to play an important role (Hurt-Camejo, E. et al. 1997. *Arterioscler Thromb Vasc Biol.* 17:1011–1017; Williams, K. J., and I. Tabas. 1995. *Arterioscier. Thromb. Vasc Biol.* 15:551–561; Camejo, G. et al. 1988. *Arteriosclerosis.* 8:368–377; and Hurt, E., and G. Camejo. 1987. *Atherosclerosis.* 67:115–126). First, purified arterial proteoglycans, especially those from lesion-prone sites (Cardoso, L. E., and P. A. Mourao. 1994. *Arterioscler. Thromb.* 14:115–124; and Ismail, N. et al. 1994. *Atherosclerosis.* 105:79–87), bind atherogenic lipoproteins in vitro, particularly LDL from patients with coronary artery disease (Lindén, T. et al. 1989. *Eur. J Clin. Invest.* 19:38–44). LDL binds with high affinity to dermatan sulfate and chondroitin sulfate proteoglycans produced by proliferating smooth muscle cells (Camejo, G. et al. 1993. *J. Biol Chem.* 268:1413–1437). Second, proteoglycans are a major component of the artery wall extracellular matrix and are available to participate in the interactions of lipoproteins in the earliest stages of atherogenesis. Third, retained apo-B immunologically co-localizes with proteoglycans in early and developed lesions (Walton, K., and N. Williamson. 1968. *J. Atheroscler. Res.* 8:599–624; Hoff, H., and G. Bond. 1983. *Artery.* 12:104–116; Hoff, H. F., and W. D. Wagner. 1986. *Atherosclerosis.* 61:231–236; Nievelstein-Post, P. et al. 1994. *Arterioscler. Thromb.* 14:1151–1161; and Galis, Z. et al. 1993. *Am J. Pathol.* 142:1432–1438). The observation that the arterial wall content of these proteoglycans increases during atherosclerosis and correlates with an increased accumulation of aortic cholesterol also supports the potential importance of the interaction between LDL and proteoglycans (Hoff, H. F., and W. D. Wagner. 1986. *Atherosclerosis.* 61:231–236; Merrilees, M. et al. 1990. *Arteriosclerosis.* 81:245–254).

Proteoglycans contain long carbohydrate side-chains of glycosaminoglycans, which are covalently attached to a core protein by a glycosidic linkage. The glycosaminoglycans consist of repeating disaccharide units, all bearing negatively charged groups, usually sulfate or carbohydrate groups. In vitro, LDL bind with high affinity to many proteoglycans found in the artery wall, including dermatan sulfate proteoglycans (e.g., biglycan) and chondroitin sulfate proteoglycans (e.g., versican), which are produced by smooth muscle cells in response to PDGF or TGFβ (Schonherr, E. et al. 1991. *J. Biol. Chem.* 266:17640–17647; and Schönherr, E. et al. 1993. *Arterioscler. Thromb.* 13:1026–1036). The interaction between LDL and proteoglycans have been hypothesized to involve clusters of basic amino acids in apo-B100, the protein moiety of LDL, that interact with the negatively charged glycosaminoglycan proteoglycans (Mahley, R. et al. 1979. *Biochem. Biophys. Acta.* 575:81–91; Carnejo, G. et al. 1988. *Arteriosclerosis.* 8:368–377; Weisgraber, K., and S. Rall, Jr. 1987. *J. Biol. Chem.* 262:11097–11103; and Hirose, N. et al. 1987. *Biochemistry.* 26:5505–5512) or by bridging molecules such as apo-E or lipoprotein lipase (Williams, K. J., and I. Tabas. 1995. *Arterioscier. Thromb. Vasc. Biol.* 15:551–561).

Isolation of large fragments of apo-B100 from different regions characterized by concentrations of positive clusters indicated that up to eight specific regions in apo-B100 bind proteoglycans (Camejo, G. et al. 1988. *Arteriosclerosis.* 8:368–377; Weisgraber, K., and S. Rall, Jr. 1987. *J. Biol. Chem.* 262:11097–11103; and Hirose, N. et al. 1987. *Biochemistry.* 26:5505–5512). Weisgraber, K., and S. Rall, Jr. 1987. *J. Biol. Chem.* 262:11097–11103 identified two fragments, residues 3134–3209 and 3356–3489, that bind to heparin with the highest affinity. Recently Camejo and coworkers confirmed this finding and proposed that residues 3147–3157 and 3359–3367 may act cooperatively in the association with proteoglycans (Hurt-Camejo, E. et al. 1997. *Arterioscler Thromb Vasc Biol.* 17:1011–1017; and Olsson, U. et al. 1997. *Arterioscler. Throm. Vasc. Biol.* 17:149–155). However, because these studies were carried out with delipidated apo-B fragments in the presence of urea or with short synthetic apo-B peptides, it is not clear which of the binding sites are functionally expressed on the surface of LDL particles. Some or many of these postulated glycosaminoglycan-binding sites may not be functional when apo-B is associated with LDL. For example, apo-E has two heparin-binding sites, but only one binds to heparin when apo-E is completed with phospholipid (Weisgraber, K. et al. 1986. *J. Biol Chen* 261:2068–2076). This heparin-binding site coincides with the LDL receptor-binding site of apo-E.

Although eight potential glycosaminoglycan-binding sites have been identified in apo-B100 (Camejo, G. et al. 1988. *Arteriosclerosis*. 8:368–377; Weisgraber, K., and S. Rall, Jr. 1987. *J. Biol. Chem.* 262:11097–11103; and Hirose, N. et al. 1987. *Biochemistry*. 26:5505–5512), it was not known which of them participate in the physiological binding of LDL to proteoglycans. Previously, we have demonstrated, in conjunction with others, that Site B (residues 3359–3369) is the LDL receptor-binding site, and in the study which generated the present invention we found that it is also the primary binding site to proteoglycans.

Modification of LDL potentially exposes the other proteoglycan-binding sites. Paananen and Kovanen (Paananen, K., and P. T. Kovanene. 1994. *J. Biol. Chem.* 269:2023–2031) noted that proteolysis of apo-B100 strengthened the binding of LDL to proteoglycans, suggesting the exposure of buried heparin binding sites. Likewise, when LDL are fused by sphingomyelinase treatment, the modified lipoproteins bind more avidly to proteoglycans. The finding that multiple heparin molecules bind to LDL (Cardin, A. et al. 1987. *Biochemistry*. 26:5513–5518) may also be explained by a cooperative effect of heparin binding to one site that triggers a conformational change in apo-B100 that enables other sites to participate in the interaction. Thus, the initial interaction with proteoglycans may induce structural alterations of the LDL that expose heparin/proteoglycan-binding sites that may contribute to the intramural retention of LDL after the initial interaction with the primary binding site.

The interaction between LDL and the LDL receptor plays a major role in determining plasma cholesterol levels in humans and other mammalian species (Goldstein, J. et al. 1985. *Annu. Rev. Cell Biol.* 1:1–39). Apo-B100 is the major protein component of LDL and is responsible for the binding of these lipoproteins to the LDL receptor (Innerarity, T. et al. 1990. *J. Lipid Res.* 31:1337–1349). The relevance of this catabolic pathway is best illustrated by the genetic disorders familial hypercholesterolemia (FH) and familial defective apo-B100 (FDB), in which high levels of LDL accumulate in the circulation because mutations in the LDL receptor (FH) or in the ligand (FDB) disrupt the binding of LDL to its receptor (Innerarity, T. et al. 1990. *J. Lipid Res.* 31:1337–1349). Many different mutations of the LDL receptor cause FH (Hobbs, H. et al. 1992. *Hum. Mutat.* 1:445–466), but FDB is associated with a single site mutation, the substitution of glutamine (Innerarity, T. et al. 1987. *Proc. Natl. Acad. Sci. USA*. 84:6919–6923) or, in a few cases, tryptophan (Gaffney, D. et al. 1995. *Arterioscler. Thromb. Vasc. Biol.* 15:1025–1029) for the normally occurring arginine at residue 3500 of apo-B100. With the exception of an arginine-3531 to cysteine mutation (Pullinger, C. et al. 1995. *J. Clin. Invest.* 95:1225–1234), which is associated with a minor decrease in LDL receptor binding, extensive searches have not found any other mutations of apo-B100 that cause defective receptor binding of LDL (Pullinger, C. et al. 1995. *J. Clin. Invest.* 95:1225–1234). The FDB mutation occurs at an estimated frequency of 1/500 in the normal population and is therefore one of the most common known single-gene defects causing an inherited abnormality (Innerarity, T. et al. 1990. *J. Lipid Res.* 31:1337–1349).

Much attention has focused on understanding the molecular interaction between apo-B100 and the LDL receptor. The structural and functional domains of the LDL receptor have been defined in detail (Hobbs, H. et al. 1992. *Hum. Mutat.* 1:445–466), but much less is understood about the receptor-binding domain of apo-B100, because of its large size and insolubility in aqueous buffer. Furthermore, both the lipid composition and the conformation of apo-B100 appear to be crucial to its function as an effective ligand for the LDL receptor, since apo-B100 binds to the LDL receptor only after the conversion of large VLDL to smaller LDL (Goldstein, J. et al. 1985. *Annu. Rev. Cell Biol.* 1:1–39).

Selective chemical modification of the apo-B100 of LDL demonstrated that the basic amino acids arginine and lysine were important in the interaction of LDL with its receptor (Mahley, R. et al. 1977. *J. Biol. Chem.* 252:7279–7287; and Weisgraber, K. et al. 1978. *J. Biol. Chem.* 253:9053–9062). Once apo-B100 was sequenced, several regions enriched in arginine and lysine residues became candidates for receptor binding, including Site A (residues 3147–3157) and Site B (residues 3359–3367) (Knott, T. et al. 1985. *Science*. 230:37–43).

While it had been hypothesized that LDL-proteoglycan binding was possibly important to the formation of atherosclerotic lesions through the retention of lipoproteins in the subendothelium, this hypothesis has not been empirically demonstrated in the art. Moreover, there have been six obstacles which have prevented other researchers from demonstrating the mechanism by which atherogenesis occurs and using this information to combat atherosclerosis. First, there have been eight potential sites identified in the apo-B100 protein, any one or several of which could have been responsible for proteoglycans trapping LDL in the subendothelium. Second, it has been unknown which potential sites in the apo-B100 are exposed to the surface of the LDL particles and which are buried within the lipid core. Third, there has been evidence that some of the potential proteoglycan binding sites on apo-B100 may work cooperatively, creating the possibility that blocking proteoglycan binding at any single site might not have proven both necessary and sufficient to eliminate LDL retention in the subendothelium. Fourth, the modification of LDL has been shown in some cases to expose new proteoglycan binding sites to the surface. Fifth, any disruption to LDL proteoglycan binding had the potential to disrupt LDL receptor binding, which would serve to disrupt the natural clearance of LDL from blood, raise serum cholesterol levels, and potentially result in a condition similar to familial hypercholesterolemia. Sixth, it has not been possible to use site-directed mutagenesis and express the entire mutated apo-B100 proteins as LDL in order to define the proteoglycan-binding sites on LDL.

SUMMARY OF THE INVENTION

We have discovered that the amino acids of Site B in the apo-B100 protein are responsible for conferring proteoglycan binding activity on LDL. Recombinant LDL in which lysine$_{3363}$ in apo-B100 was changed to glutamic acid has severely defective proteoglycan binding activity but normal LDL receptor-binding activity. Thus, the proteoglycan-binding and the receptor-binding activities in LDL can be separated by the introduction of a single point mutations into the apo-B100 protein, indicating that pharmaceutical strategies for disrupting LDL-proteoglycan binding need not inhibit LDL receptor binding.

Moreover, we have demonstrated for the first time in vivo that LDL-proteoglycan binding is necessary to the formation of atherosclerotic lesions and the onset of atherosclerosis.

Transgenic mice expressing the mutant RK3359–3369SA apo-B100 LDL, which is defective for proteoglycan binding, was found to have strikingly less atherosclerosis than mice expressing the wild-type recombinant LDL, when both were fed a high cholesterol diet. These results demonstrate that disruption of LDL-proteoglycan binding at Site B in the apo-B100 protein is a credible target for pharmaceutical intervention for the reduction and elimination of atherosclerosis.

The present invention relates to the prevention of atherosclerosis through the modulation of LDL-proteoglycan binding at Site B (amino acids 3359–3369) of the apo-B100 protein in LDL. The invention encompasses apo-B100 proteins with mutations in Site B and which exhibit reduced binding to proteoglycans, fragments of these proteins containing Site B, and LDL particles comprising such mutants. The invention includes purified apo-B100 proteins comprising a mutation in Site B which results in reduced LDL-proteoglycan binding activity while maintaining LDL/LDL receptor binding (proteoglycan⁻receptor⁺mutant), including, for example, the K3363E mutation. The inventions also includes polypeptide fragments of these proteins which comprise the amino acid sequence of Site B in the apo-B100 protein of the invention, wherein said Site B is flanked on at least one side by a contiguous sequence of amino acids which is directly adjacent to Site B in the wild-type human apo-B100 sequence. The invention encompasses LDL particles and other lipoproteins which comprise an apo-B100 protein or protein fragment of the invention.

Accordingly, in certain embodiments, the invention provides mutant apo-B100 proteins and mutant apo-B100 polypeptide fragments, as well as LDL particles and other lipoproteins comprising a mutant apo-B100 protein or polypeptide fragment, which comprise a mutant Site B selected from one of the following Site B sequences:

$Thr_{3358}$-$Arg_{3359}$-$Leu_{3360}$-$Thr_{3361}$-$Arg_{3362}$-$Glu_{3363}$-$Arg_{3364}$-$Gly_{3365}$-$Leu_{3366}$-$Lys_{3367}$(SEQ ID NO:1);

$Thr_{3358}$-$Arg_{3359}$-$Leu_{3360}$-$Thr_{3361}$-$Arg_{3362}$-$Asp_{3363}$-$Arg_{3364}$-$Gly_{3365}$-$Leu_{3366}$-$Lys_{3367}$(SEQ ID NO:2);

$Thr_{3358}$-$Arg_{3359}$-$Leu_{3360}$-$Thr_{3361}$-$Arg_{3362}$-$Ala_{3363}$-$Arg_{3364}$-$Gly_{3365}$-$Leu_{3366}$-$Lys_{3367}$(SEQ ID NO:3);

$Thr_{3358}$-$Arg_{3359}$-$Leu_{3360}$-$Thr_{3361}$-$Arg_{3362}$-$Thr_{3363}$-$Arg_{3364}$-$Gly_{3365}$-$Leu_{3366}$-$Lys_{3367}$(SEQ ID NO:4);

$Thr_{3358}$-$Arg_{3359}$-$Leu_{3360}$-$Thr_{3361}$-$Arg_{3362}$-$Ser_{3363}$-$Arg_{3364}$-$Gly_{3365}$-$Leu_{3366}$-$Lys_{3367}$(SEQ ID NO:5);

$Thr_{3358}$-$Arg_{3359}$-$Leu_{3360}$-$Thr_{3361}$-$Arg_{3362}$-$Gly_{3363}$-$Arg_{3364}$-$Gly_{3365}$-$Leu_{3366}$-$Lys_{3367}$(SEQ ID NO:6);

$Thr_{3358}$-$Arg_{3359}$-$Leu_{3360}$-$Thr_{3361}$-$Gly_{3362}$-$Lys_{3363}$-$Arg_{3364}$-$Gly_{3365}$-$Leu_{3366}$-$Lys_{3367}$(SEQ ID NO:7);

$Thr_{3358}$-$Arg_{3359}$-$Leu_{3360}$-$Thr_{3361}$-$Asp_{3362}$-$Lys_{3363}$-$Arg_{3364}$-$Gly_{3365}$-$Leu_{3366}$-$Lys_{3367}$(SEQ ID NO:8);

$Thr_{3358}$-$Arg_{3359}$-$Leu_{3360}$-$Thr_{3361}$-$Arg_{3362}$-$LYS_{3363}$-$Glu_{3364}$-$Gly_{3365}$-$Leu_{3366}$-$Lys_{3367}$(SEQ ID NO:9);

$Thr_{3358}$-$Arg_{3359}$-$Leu_{3360}$-$Thr_{3361}$-$Arg_{3362}$-$Lys_{3363}$-$Asp_{3364}$-$Gly_{3365}$-$Leu_{3366}$-$Lys_{3367}$(SEQ ID NO:10);

$Thr_{3358}$-$Glu_{3359}$-$Leu_{3360}$-$Thr_{3361}$-$Arg_{3362}$-$Lys_{3363}$-$Arg_{3364}$-$Gly_{3365}$-$Leu_{3366}$-$Lys_{3367}$(SEQ ID NO:11); and $Thr_{3358}$-$Asp_{3359}$-$Leu_{3360}$-$Thr_{3361}$-$Arg_{3362}$-$Lys_{3363}$-$Arg_{3364}$-$Gly_{3365}$-$Leu_{3366}$-$Lys_{3367}$(SEQ ID NO:12); as well as Site B sequences with deletions, such as:

$Thr_{3358}$-$Arg_{3359}$-$Leu_{3360}$-$Thr_{3361}$-$Arg_{3362}$-$Arg_{3364}$-$Gly_{3365}$-$Leu_{3366}$-$Lys_{3367}$(SEQ ID NO:13);

$Thr_{3358}$-$Arg_{3359}$-$Leu_{3360}$-$Thr_{3361}$-$Lys_{3363}$-$Arg_{3364}$-$Gly_{3365}$-$Leu_{3366}$-$Lys_{3367}$(SEQ ID NO:14); and $Thr_{3358}$-$Arg_{3359}$-$Leu_{3360}$-$Thr_{3361}$-$Arg_{3362}$-$Lys_{3363}$-$Gly_{3365}$-$Leu_{3366}$-$Lys_{3367}$(SEQ ID NO:15); and Site B sequences which include insertions, such as:

$Thr_{3358}$-$Arg_{3359}$-$Leu_{3360}$-$Thr_{3361}$-$Arg_{3362}$-$Glu$-$Lys_{3363}$-$Arg_{3364}$-$Gly_{3365}$-$Leu_{3366}$-$Lys_{3367}$(SEQ ID NO:16);

$Thr_{3358}$-$Arg_{3359}$-$Leu_{3360}$-$Thr_{3361}$-$Arg_{3362}$-$Lys_{3363}$-$Glu$-$Arg_{3364}$-$Gly_{3365}$-$Leu_{3366}$-$Lys_{3367}$(SEQ ID NO:17);

$Thr_{3358}$-$Arg_{3359}$-$Leu_{3360}$-$Thr_{3361}$-$Arg_{3362}$-$Asp$-$Lys_{3363}$-$Arg_{3364}$-$Gly_{3365}$-$Leu_{3366}$-$Lys_{3367}$(SEQ ID NO:18); and $Thr_{3358}$-$Arg_{3359}$-$Leu_{3360}$-$Thr_{3361}$-$Arg_{3362}$-$Lys_{3363}$-$Asp$-$Arg_{3364}$-$Gly_{3365}$-$Leu_{3366\text{-}Lys3367}$(SEQ ID NO:19).

The invention also includes antibodies which bind to antigenic determinants comprising Site B of the mutant apo-B100 proteins of the invention, including antibody compositions which bind to an antigenic determinant in an apo-B100 protein or protein fragment of the invention, wherein said antigenic determinant is not present in the wild-type human apo-B100 protein.

The invention also encompasses polynucleotides encoding the mutant apo-B100 proteins of the invention, targeting vectors and methods for creating mutant apo-B100 genes of the invention. The invention includes polynucleotides which encode an apo-B 100 protein or protein fragment of the invention, as well as cells comprising a polynucleotide of the invention or expressing an apo-B100 protein or protein fragment of the invention. The invention also includes non-human animals and mammals which comprise a polynucleotide of the invention or express an LDL, apo-B100 protein, or protein fragment of the invention.

The invention encompasses methods for preventing or reducing the severity of atherosclerosis in an animal or mammal, comprising the step of expressing a polynucleotide, LDL, apo-B100 protein, or protein fragment of the invention. Normally, a polynucleotide encoding an apo-B100 protein or protein fragment of the invention is transduced into a cell. The cell may be transduced ex vivo, then transferred into the animal or mammal, or the cell may be transduced in situ.

The present invention further encompasses methods of screening for and identifying inhibitors of LDL-proteoglycan binding, including drug screening assays based on simple LDL-proteoglycan binding, high through-put drug screening assays based on LDL-proteoglycan binding, two step LDL/proteoglycan and LDL/LDL-receptor binding assays, and in transgenic animals which express recombinant LDL.

The present invention encompasses methods for identifying inhibitors of LDL-proteoglycan binding, comprising the steps of:

(a) incubating a mixture comprising (i) proteoglycan, (ii) LDL, and (iii) a candidate compound, under conditions wherein LDL binds to proteoglycan to form an LDL-proteoglycan complex in the absence of said candidate compound;

(b) determining any difference between the amount of LDL-proteoglycan complex present in:
(i) the mixture prepared in step (a), and
(ii) a control mixture comprising said proteoglycan and said LDL in the absence of said candidate compound; and optionally (c) correlating any difference determined in step (b) with said candidate compound's ability to affect LDL-proteoglycan binding.

The present invention also encompasses identifying compounds which affect LDL-proteoglycan binding, which do not substantially affect LDL receptor binding, which further comprising the steps of:

(d) incubating a mixture comprising (i) LDL receptor, (ii) LDL, and (iii) a candidate compound that affects LDL-proteoglycan binding identified in step (c), under conditions wherein LDL binds to LDL receptor to form an LDL-LDL receptor complex in the absence of said inhibitor of LDL-proteoglycan binding;

(e) determining any difference between the amount of LDL-LDL receptor complex present in:
   (i) the mixture prepared in step (d), and
   (ii) a control mixture comprising said LDL receptor and said LDL in the absence of said inhibitor of LDL-proteoglycan binding; and optionally (f) correlating any difference determined in step (e) with the LDL-LDL receptor binding activity of said candidate compound that affects LDL-proteoglycan binding.

In accordance with the instant invention, either the LDL or the proteoglycan of step (a) may be adhered to a solid support. Additionally, where the LDL is adhered to a solid support, the proteoglycan may be labeled, or where the proteoglycan is adhered to a solid support, the LDL may be labeled.

The invention further encompasses methods for identifying compounds which modulate atherosclerosis and/ LDL-proteoglycan binding in vivo, comprising the steps of:

(a) administering a candidate compound to a transgenic non-human animal which expresses a human apo-B gene, under conditions wherein measurable atherosclerotic lesions form in the arteries of said animal in the absence of said candidate compound;

(b) determining any difference between the extent of atherosclerosis present in:
   (i) the animal of step (a), and
   (ii) a control transgenic non-human animal in the absence of said candidate compound; and optionally (c) correlating any difference determined in step (b) with the said candidate compound's ability to modulate atherosclerosis in vivo.

The present invention further encompasses the compounds identified by the screening methods of the invention, including the compounds which affect, modulate, stimulate or inhibit of LDL-proteoglycan binding identified by the methods for identifying compounds that affect LDL-proteoglycan binding, as well as the compounds that affect, modulate, stimulate, or inhibit LDL-proteoglycan binding, which do not substantially affect LDL receptor binding identified by the methods for identifying inhibitors of LDL-proteoglycan binding, which do not eliminate LDL receptor binding, and the compounds which modulate, stimulate, or inhibit atherosclerosis in vivo identified by the methods for identifying compounds which modulate atherosclerosis in vivo. In addition the invention encompasses methods of inhibiting atherosclerosis in a human comprising administering to the human an agent that inhibits LDL-proteoglycan binding, or any of the other compounds identified by the methods of the invention.

BRIEF DESCRIPTION OF THE DRAWINGS

FIG. 1 is a half tone reproduction of a Coomassie staining and western analysis of recombinant LDL. Recombinant LDL (d=1.02–1.05 g/ml) from four lines of human apo-B transgenic mice were isolated by sequential ultracentrifugation and subjected to immunoaffinity chromatography to remove endogenous apo-B and apo-E. Five micrograms of apo-B100 from human plasma LDL (lane 1) or recombinant LDL: control LDL (lane 2), R3500Q LDL (lane 3), RK3359–3369SA LDL (lane 4), and K3363E LDL (lane 5) were analyzed by SDS-PAGE with 3–15% gels (FIG. 1A). One microgram each of unpurified LDL (lane 1) and control LDL (lane 2), R3500Q LDL (lane 3), RK3359–3369SA LDL (lane 4), and K3363E LDL (lane 5) were analyzed by western blots with monoclonal antibody 1 D 1 against human apo-B (FIG. 1B) and polyclonal antibodies against mouse apo-B (FIG. 1C) or mouse apo-E (FIG. 1D).

Figure 2:
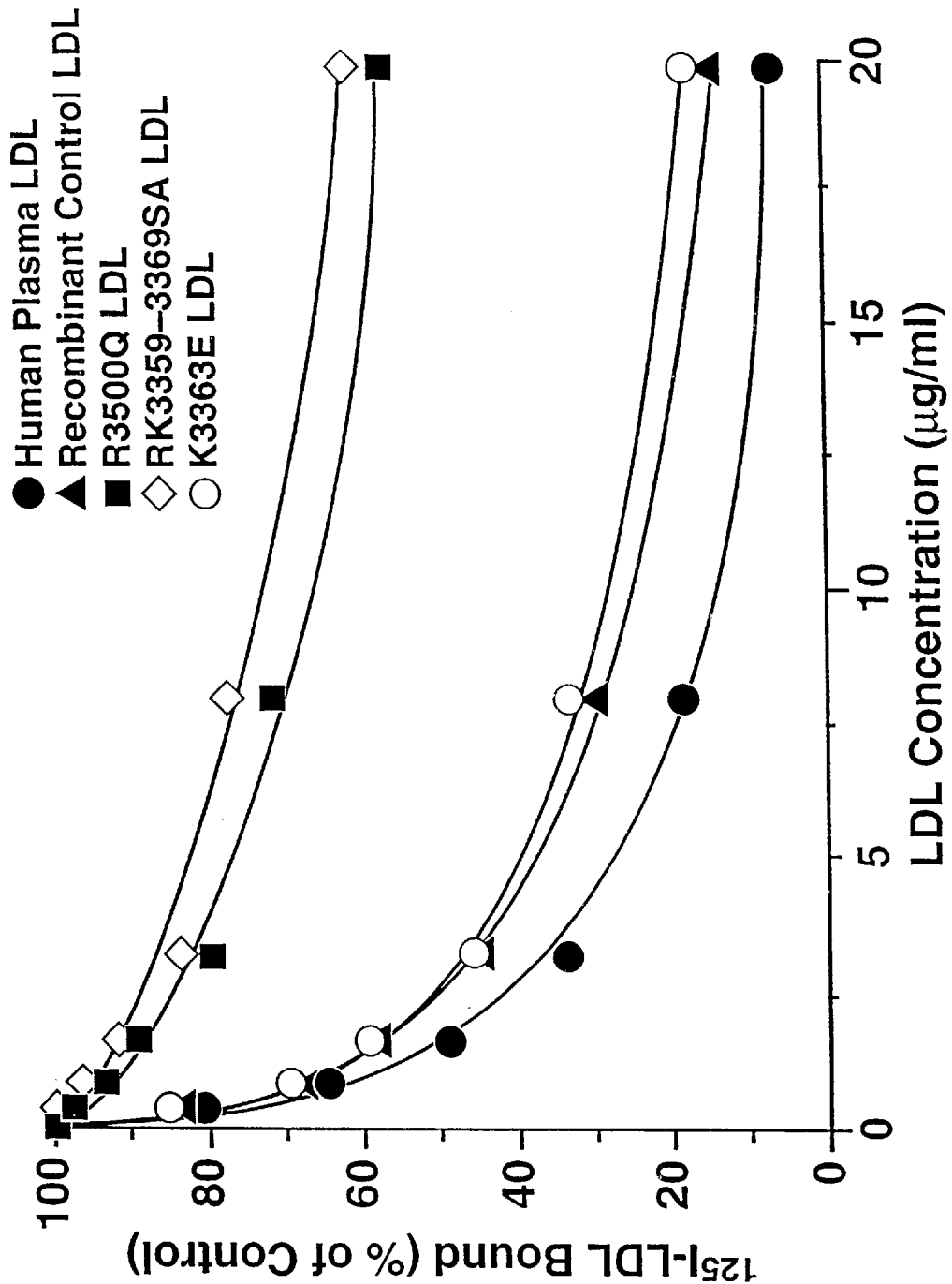
FIG. 2 is a graph demonstrating a competitive binding assay of recombinant LDL. The abilities of recombinant control LDL (closed triangle), R3500Q LDL (closed square), RK3359–3369SA LDL (open diamond), and K3363E LDL (open circle) to compete with $^{125}$I-labeled human plasma LDL (2 µg/ml) for binding to LDL receptors on normal human fibroblasts were determined. The recombinant lipoproteins were isolated from 15 mice, and endogenous apo-E and apo-B were removed. Competitor LDL were added at the indicated concentrations to normal human fibroblasts, and the amount of $^{125}$I-LDL bound to the fibroblasts was measured after a 3-h incubation. The results represent the average of data from three independent experiments performed with freshly isolated LDL for each experiment human plasma LDL (closed circle) was included as a control.

The wild-type recombinant LDL mouse and the RK3359–3369SA LDL mouse had plasma cholesterol levels of 678 and 616 mg/dl, respectively.

DISCLOSURE OF THE INVENTION

The practice of the present invention encompasses conventional techniques of chemistry, immunology, molecular biology, biochemistry, protein chemistry, and recombinant DNA technology, which are within the skill of the art. Such techniques are explained fully in the literature. See, e.g., *Oligonucleotide Synthesis* (M. Gait ed. 1984); *Nucleic Acid Hybridization* (B. Hames & S. Higgins, eds., 1984); Sambrook, Fritsch & Maniatis, *Molecular Cloning: A Laboratory Manual*, Second Edition (1989); *PCR Technology* (H. A. Erlich ed., Stockton Press); R. Scope, *Protein Purification Principles and Practice* (Springer-Verlag); and the series *Methods in Enzymology* (S. Colowick and N. Kaplan eds., Academic Press, Inc.).

Definitions:

The terms "LDL" or "low density lipoprotein" refers to a particle with a diameter of approximately 22 nm and a mass of about three million Dalton found in plasma. LDL is comprised of a highly hydrophobic core of approximately 1500 cholesteryl ester molecules surrounded by a shell of phospholipids, unesterified cholesterol, and a single apo-B100 protein. LDL is often differentiated and separated from other plasma lipoproteins by its density of 1.019 to 1.063 g/ml through ultracentrifugation as described in Example 4. As used herein the term "LDL" embraces lipoprotein particles comprising a mutant apo-B100 protein, as well as lipids which do not naturally occur in LDL and labels, all of which may change the physical properties listed above. In all cases an LDL particle contains only one apolipoprotein, a apo-B100 protein or fragment thereof, and contains a lipid core which is predominantly cholesteryl ester.

The "apo-B100 protein" resides in the outer shell of very low density lipoproteins (VLDL), intermediate density lipoproteins (IDL), and low density lipoproteins (LDL). The complete sequence and identification of structural domains of human apo-B100 protein is found in Knott, T. et al 1986. *Nature* 323:734–738.

Apo-B100 is the component of LDL which binds specifically to the "LDL receptor" on the plasma membrane of non-hepatic cells. The LDL receptors are localized in specialized regions called coated pits, where the "LDL/LDL receptor complex" is internalized through endocytosis, delivering cholesterol to the cell. As used herein the "LDL receptor" and any resulting "LDL/LDL receptor complex" need not contain any portion of the native LDL receptor which is not needed to achieve LDL-binding. Thus, only a sufficient portion of the 292 amino-terminal amino acid LDL-binding domain of the native LDL receptor and any other domains which are necessary to confer binding to LDL need be present in an "LDL receptor."

As used herein, the term "purified apo-B100 protein" refers to an apo-B100 protein isolated from a lipoprotein, including wild-type apo-B100, mutant apo-B100 and protein fragments thereof, which is essentially free, i.e., contains less than about 50%, preferably less than about 30%, and more preferably less than about 10%, even more preferably less than about 5%, and still more preferably less than about 1% of the lipids with which an apo-B100 protein is normally associated in a lipoprotein.

As used herein the term "Site B" refers to amino acids from about 3359 to about 3369 of the human apo-B100 protein The terms "human recombinant LDL" and "recombinant LDL" are used interchangeably herein to refer to LDL populations comprising LDL particles derived from a non-human animal which contains a human apo-B100 protein. The human apo-B100 proteins contained within a recombinant LDL may be wild-type apo-B100 protein. Without express mention, the human apo-B100 protein of a recombinant LDL may also have a leucine in place of the glutamine residue at position 2153, which abolishes the formation of apo-B48, resulting in a higher yield of recombinant apo-B100 LDL. In addition the human apo-B100 proteins of recombinant LDL may have other mutations which are expressly noted in their name (e.g., K3363E LDL). In addition the term "recombinant LDL" embraces any LDL reagent which comprises at least a fragment of a recombinant apo-B100 protein and maintains the LDL-proteoglycan binding activity of at least 60% of wild-type levels, preferably at least 70%, more preferably at least 80%, still more preferably 90%, most preferably at essentially 100% of wild-type LDL-proteoglycan binding activity. The phrase "recombinant control LDL" is used herein to refer to LDL, containing a human apo-B100 protein in which the glutamine at amino acid position 2153 has been replaced with a leucine.

As used herein the term "R3500Q" refers to a human apo-B100 protein in which the naturally-occurring arginine at residue 3500 of the human apo-B100 protein has been replaced with a glutamine residue. The term is also used to refer to genes and plasmids which encode the R3500Q mutant apo-B100 protein, as well as recombinant LDL which comprises the mutant protein and transgenic mice or other non-human animals which express the R3500Q recombinant LDL.

As used herein the term "K3363E" refers to a human apo-B100 protein wherein the naturally-occurring lysine at residue 3363 of the human apo-B100 protein has been replaced with a glutamic acid residue. The term is also used to refer to genes and plasmids which encode the K3363E mutant apo-B100 protein, as well as recombinant LDL which comprises the mutant protein and transgenic mice or other non-human animals which express the K3363E recombinant LDL.

As used herein the term "RK3359–3369SA" refers to a human apo-B100 protein in which the basic amino acids in Site B (residues 3359–3369) were converted to neutral amino acids with all of the arginine residues being converted to serines and the lysine residues being converted to alanines. The term is also used to refer to genes and plasmids which encode the RK3359–3369SA mutant apo-B100 protein, as well as recombinant LDL which comprises the mutant protein and transgenic mice or other non-human animals which express the RK3359–3369SA recombinant LDL.

As used herein the term "proteoglycan⁻receptor⁺" is used to refer mutant apo-B100 proteins, fragments thereof as well as LDL comprising these polypeptides and transgenic non-human animal strains which express these proteins. A proteoglycan⁻receptor⁺apo-B100 protein when present in an LDL particle reduces proteoglycan binding of that LDL particle by at least 50%, preferably by at least 60%, more preferably by at least 70%, still more preferably by at least 80%, even more preferably by at least 90%, most preferably by 95% or greater. Proteoglycan binding may be assayed by any method known in the art. See, for example, the method described in Example 8. In addition a proteoglycan⁻receptor⁺apo-B100 protein when present in an LDL particle confers LDL receptor binding activity to that LDL particle of at least 60% of wild-type levels, preferably at least 70%, more preferably at least 80%, still more preferably 90%, most preferably at essentially 100% of wild-type LDL receptor binding activity.

The amino acid sequence of the wild-type human apo-B100 protein from amino acid 3358 to 3367 is as follows:

$Thr_{3358}$-$Arg_{3359}$-$Leu_{3360}$-$Thr_{3361}$-$Arg_{3362}$-$Lys_{3363}$-$Arg_{3364}$-$Gly_{3365}$-$Leu_{3366}$-$Lys_{3367}$(SEQ ID NO:20).

The proteoglycan⁻receptor⁺mutant apo-B100 proteins of the invention involve substitutions or deletions at the following four amino acid positions: $Lys_{3363}$, $Arg_{3362}$, $Arg_{3364}$, and $Arg_{3359}$. A proteoglycan⁻receptor⁺mutant of the invention can be constructed by the substitution or deletion of any single one of these amino acids, any combination or them or all four of the amino acids in positions 3363, 3362, 3364, and 3359. Preferably two or fewer of these amino acids are substituted or deleted, more preferably only a single amino acid is substituted or deleted. When only a single amino acid is chosen to be substituted or deleted, preferably the amino acid which is substituted or deleted is one of positions 3363, 3362, and 3364, more preferably position 3363. While any amino acid can be used in a substitution, preferably the new amino acid is chosen from the group consisting of Gly, Ala, Val, Leu, Ile, Phe, Tyr, Trp, Cys, Met, Asn, Gln, Asp, and Glu, more preferably the new amino acid is either Asp or Glu.

In addition to deletions and substitution, a proteoglycan⁻receptor⁺apo-B100 proteins can be formed by additions to the amino acid sequence. Additions are usually only a single amino acid, and can be made to one or more of the following locations: between 3358 and 3359, between 3359 and 3360, between 3361 and 3362, between 3362 and 3363, between 3363 and 3364, and between 3364 and 3365. Preferably additional amino acids are added to two or fewer of these sites, more preferably an addition is made to only one of these sites. When only a single position is chosen for an addition preferably that site is either between 3362 and 3363, or between 3363 and 3364. While any amino acid may be added for these additions, preferably amino acids for addition are chosen from the following list Gly, Ala, Val, Leu, Ile, Phe, Tyr, Trp, Cys, Met, Asn, Gln, Asp, and Glu, more preferably the new amino acid is Ala, Ser, Thr, Gln, Asp or Glu, even more preferably the new amino acid is Asp or Glu. It should be noted that combinations of the additions, deletions and substitutions described can be employed to construct a proteoglycan⁻receptor⁺apo-B100 protein. These changes to the native protein may be achieved by any method known in the art, including chemical synthesis or modification. However, expression of recombinant apo-B100 gene made by site-directed mutagenesis as demonstrated, for example, in Examples 1–3 is preferred.

The following are the amino acid sequences from position 3358 to position 3367 for a list of preferred proteoglycan⁻receptor⁺apo-B100 protein mutants:

$Thr_{3358}$-$Arg_{3359}$-$Leu_{3360}$-$Thr_{3361}$-$Arg_{3362}$-$Glu_{3363}$-$Arg_{3364}$-$Gly_{3365}$-$Leu_{3366}$-$Lys_{3367}$(SEQ ID NO:1)

$Thr_{3358}$-$Arg_{3359}$-$Leu_{3360}$-$Thr_{3361}$-$Arg_{3362}$-$Asp_{3363}$-$Arg_{3364}$-$Gly_{3365}$-$Leu_{3366}$-$Lys_{3367}$(SEQ ID NO:2)

$Thr_{3358}$-$Arg_{3359}$-$Leu_{3360}$-$Thr_{3361}$-$Arg_{3362}$-$Ala_{3363}$-$Arg_{3364}$-$Gly_{3365}$-$Leu_{3366}$-$Lys_{3367}$(SEQ ID NO:3)

$Thr_{3358}$-$Arg_{3359}$-$Leu_{3360}$-$Thr_{3361}$-$Arg_{3362}$-$Thr_{3363}$-$Arg_{3364}$-$Gly_{3365}$-$Leu_{3366}$-$Lys_{3367}$(SEQ ID NO:4)

$Thr_{3358}$-$Arg_{3359}$-$Leu_{3360}$-$Thr_{3361}$-$Arg_{3362}$-$Ser_{3363}$-$Arg_{3364}$-$Gly_{3365}$-$Leu_{3366}$-$Lys_{3367}$(SEQ ID NO:5)

$Thr_{3358}$-$Arg_{3359}$-$Leu_{3360}$-$Thr_{3361}$-$Arg_{3362}$-$Gln_{3363}$-$Arg_{3364}$-$Gly_{3365}$-$Leu_{3366}$-$Lys_{3367}$(SEQ ID NO:6)

$Thr_{3358}$-$Arg_{3359}$-$Leu_{3360}$-$Thr_{3361}$-$Glu_{3362}$-$Lys_{3363}$-$Arg_{3364}$-$Gly_{3365}$-$Leu_{3366}$-$Lys_{3367}$(SEQ ID NO:7)

$Thr_{3358}$-$Arg_{3359}$-$Leu_{3360}$-$Thr_{3361}$-$Asp_{3362}$-$Lys_{3363}$-$Arg_{3364}$-$Gly_{3365}$-$Leu_{3366}$-$Lys_{3367}$(SEQ ID NO:8)

$Thr_{3358}$-$Arg_{3359}$-$Leu_{3360}$-$Thr_{3361}$-$Arg_{3362}$-$Lys_{3363}$-$Glu_{3364}$-$Gly_{3365}$-$Leu_{3366}$-$Lys_{3367}$(SEQ ID NO:9)

$Thr_{3358}$-$Arg_{3359}$-$Leu_{3360}$-$Thr_{3361}$-$Arg_{3362}$-$Lys_{3363}$-$Asp_{3364}$-$Gly_{3365}$-$Leu_{3366}$-$Lys_{3367}$(SEQ ID NO:10)

$Thr_{3358}$-$Glu_{3359}$-$Leu_{3360}$-$Thr_{3361}$-$Arg_{3362}$-$Lys_{3363}$-$Arg_{3364}$-$Gly_{3365}$-$Leu_{3366}$-$Lys_{3367}$(SEQ ID NO:11)

$Thr_{3358}$-$Asp_{3359}$-$Leu_{3360}$-$Thr_{3361}$-$Arg_{3362}$-$Lys_{3363}$-$Arg_{3364}$-$Gly_{3365}$-$Leu_{3366}$-$Lys_{3367}$(SEQ ID NO:12)

$Thr_{3358}$-$Arg_{3359}$-$Leu_{3360}$-$Thr_{3361}$-$Arg_{3362}$-$Arg_{3364}$-$Gly_{3365}$-$Leu_{3366}$-$Lys_{3367}$(SEQ ID NO:13)

$Thr_{3358}$-$Arg_{3359}$-$Leu_{3360}$-$Thr_{3361}$-$Lys_{3363}$-$Arg_{3364}$-$Gly_{3365}$-$Leu_{3366}$-$Lys_{3367}$(SEQ ID NO:14)

$Thr_{3358}$-$Arg_{3359}$-$Leu_{3360}$-$Thr_{3361}$-$Arg_{3362}$-$Lys_{3363}$-$Gly_{3365}$-$Leu_{3366}$-$Lys_{3367}$(SEQ ID NO:15)

$Thr_{3358}$-$Arg_{3359}$-$Leu_{3360}$-$Thr_{3361}$-$Arg_{3362}$-Glu-$Lys_{3363}$-$Arg_{3364}$-$Gly_{3365}$-$Leu_{3366}$-$Lys_{3367}$(SEQ ID NO:16)

$Thr_{3358}$-$Arg_{3359}$-$Leu_{3360}$-$Thr_{3361}$-$Arg_{3362}$-$Lys_{3363}$-Glu-$Arg_{3364}$-$Gly_{3365}$-$Leu_{3366}$-$Lys_{3367}$(SEQ ID NO:17)

$Thr_{3358}$-$Arg_{3359}$-$Leu_{3360}$-$Thr_{3361}$-$Arg_{3362}$-Asp-$Lys_{3363}$-Arg3364-$Gly_{3365}$-$Leu_{3366}$-$Lys_{3367}$(SEQ ID NO:18)

$Thr_{3358}$-$Arg_{3359}$-$Leu_{3360}$-$Thr_{3361}$-$Arg_{3362}$-$Lys_{3363}$-Asp-$Arg_{3364}$-$Gly_{3365}$-$Leu_{3366}$-$Lys_{3367}$(SEQ ID NO:19), wherein the repeated dashed lines represent deletions.

The term "proteoglycan" refers to a class of compounds with a high relative molecular mass which comprise carbohydrate and protein, and are found in animal structural tissues, e.g. the ground substance of cartilage and bone. The ground substance and gel fluids of these tissues owe their viscosity and elasticity to the presence of proteoglycans. Each proteoglycan contains 40 to 80 mucopolysaccharide chains (glucosaminoglycans) usually bound to the protein via o-glycosidic linkages to serine or threonine. In contrast to the glycoproteins, the prosthetic group of proteoglycans has a relative molecular mass of 20,000 to 30,000, consisting of many (approximately 100–1000) unbranched, regularly repeating disaccharide units. The disaccharides are composed of a derivative of an amino sugar, either glucosamine or galactosamine. At least one of the sugars in the disaccharide has a negatively charged carboxylate or sulfate group. Hyaluronate, chondroitin sulfate, keratin sulfate, heparin sulfate, and heparin are the most common glucosaminoglycans. Heterogeneity of proteoglycans is due to differences in polypeptide chain length, and to the number and distribution of the attached polysaccharide chains. Microheterogenicity also exists, due to small differences in the chain lengths of the polysaccharide chains, and the distribution of sulfate residues for a particular type of proteoglycan.

As used herein, the term "atherosclerosis" refers to a disease state characterized by irregularly distributed deposits of lipid and lipoprotein in the intima of large and medium-sized arteries often covered with a fibrous cap and calcification. The terms "atherosclerotic lesions" and "atherosclerotic plaques" are used interchangeably herein to refer to these deposits.

As used herein, the term "non-human animal" refers to any non-human vertebrate, birds and more usually mammals, preferably primates, farm animals such as swine, goats, sheep, donkeys, and horses, rabbits or rodents, more preferably rats or mice. As used herein, the term "animal" is used to refer to any vertebrate, preferable a mammal. Both the terms "animal" and "mammal" expressly embrace human subjects unless preceded with the term "non-human".

As used interchangeably herein, the term "oligonucleotides", and "polynucleotides" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form.

The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, for examples of analogous linking groups, purine, pyrimidines, and sugars see for example PCT publication No. WO 95/04064. However, the polynucleotides of the invention are preferably comprised of greater than 50% conventional deoxyribose nucleotides, and most preferably greater than 90% conventional deoxyribose nucleotides. The polynucleotide sequences of the invention may be prepared by any known method, including synthetic, recombinant, ex vivo generation, or a combination thereof, as well as utilizing any purification methods known in the art.

The term "purified" is used herein to describe a polynucleotide or polynucleotide vector of the invention which has been separated from other compounds including, but not limited to other nucleic acids, and proteins (such as the enzymes used in the synthesis of the polynucleotide), or the separation of covalently closed polynucleotides from linear polynucleotides. A polynucleotide is substantially pure when at least about 60 to 75% of a sample exhibits a single polynucleotide sequence and conformation (linear versus covalently close). A substantially pure polynucleotide typically comprises about 60 to 90% weight/weight of a nucleic acid sample, more usually about 95%, and preferably is over about 99% pure. Polynucleotide purity or homogeneity may be indicated by a number of means well known in the art, such as agarose or polyacrylamide gel electrophoresis of a sample, followed by visualizing a single polynucleotide band upon staining the gel. For certain purposes higher resolution can be provided by using HPLC or other means well known in the art.

As used herein, the term "antibody" means an immunoglobulin molecule or a fragment of an immunoglobulin molecule having the ability to specifically bind to a particular antigen. Antibodies are well known to those of ordinary skill in the science of immunology. As used herein, the term "antibody" means not only intact antibody molecules but also fragments of antibody molecules retaining antigen binding ability. Such fragments are also well known in the art and are regularly employed both in vitro and in vivo. In particular, as used herein, the term "antibody" means not only intact immunoglobulin molecules of any isotype (IgA, IgG, IgE, IgD, IgM) but also the well-known active (i.e., antigen-binding) fragments $F(ab')_2$, Fab, Fv, scFv, Fd, $V_H$ and $V_L$. For antibody fragments, see, for example "Immunochemistry in Practice" (Johnstone and Thorpe, eds., 1996; Blackwell Science), p. 69. The term "antibody" further includes single chain antibodies, CDR-grafted antibodies, chimeric antibodies, humanized antibodies, and a Fab expression library. The term also includes fusion polypeptides comprising an antibody of the invention and another polypeptide or a portion of a polypeptide (a "fusion partner"). Examples of fusion partners include biological response modifiers, lymphokines, cytokines, and cell surface antigens.

As used herein, an "antigenic determinant" is the portion of an antigen molecule, in this case a mutant apo-B100 protein, that determines the specificity of the antigen-antibody reaction. An "epitope" refers to an antigenic determinant of a polypeptide. An epitope can comprise as few as 3 amino acids in a spatial conformation which is unique to the epitope. Generally an epitope consists of at least 6 such amino acids, and more usually at least 8–10 such amino acids. Methods for determining the amino acids which make up an epitope include x-ray crystallography, 2-dimensional nuclear magnetic resonance, and epitope mapping e.g. the Pepscan method described by H. Mario Geysen et al. 1984. *Proc. Natl. Acad. Sci. U.S.A.* 81:3998–4002; PCT Publication No. WO 84/03564; and PCT Publication No. WO 84/03506.

Methods for Identifying Compounds that Affect of LDL-Proteoglycan Binding

The present invention provides new assay methods for detecting, and preferably quantifying, one or more compounds that affect LDL-proteoglycan binding of interest which are present in a library of candidate compounds. Identifying compounds which inhibit LDL-proteoglycan activity is the preferred use of this assay, but it can equally be used to identify compounds which result in an increase in LDL-proteoglycan activity. The terms "assay" and "assay method," as used herein, pertain to a method of detecting the presence of (e.g., qualitative assay), and preferably quantifying (e.g., quantitative assays), the modulation of LDL-proteoglycan binding.

Assays of the present invention generally involve contacting the candidate compound of interest with a predetermined non-limiting amount of both an LDL reagent and a proteoglycan reagent, measuring the LDL-proteoglycan binding which results, and correlating the measured LDL-proteoglycan binding with the candidate compound's ability to affect or modulate LDL-proteoglycan binding. In a qualitative assay, simply determining whether the measured LDL-proteoglycan binding is above or below a threshold value (established, for example, using recombinant LDL samples with known LDL-proteoglycan binding properties) may be sufficient to establish the assay result. Typically, when the effect is an inhibition the relationship is determined from standard samples containing known amounts of a competitive inhibitor of LDL-proteoglycan binding. Such competitive inhibitors can include, depending on the assay a non-labeled LDL or proteoglycan which has normal binding activity. Thus, unless otherwise required, the term "measuring" can refer to either qualitative or quantitative determination.

The terms "agent" or "candidate compound" as used interchangeably herein, pertain to a substance which is to be measured for a possible effect on LDL-proteoglycan binding, preferably inhibitory activity. Candidate compounds may be inorganic or organic, though typically they are organic. Candidate compounds may be naturally occurring or synthetic. Candidate compounds are typically pharmacologically active "small molecules", but also include biological molecules such as amino acids, proteins, glycoproteins, lipoproteins, saccharides, polysaccharides, lipopolysaccharides, fatty acids, and nucleic acids. Examples of organic candidate compounds also include antibodies, antigens, haptens, enzymes, hormones, steroids, vitamins, oligonucleotides, and pharmacological agents.

The terms "sample" and "sample composition," as used herein, pertain to a composition which comprises one or more agents or candidate compounds of interest, or which may be processed to comprise one or more candidate compounds of interest. The samples used can be defined combinatorial libraries or undefined biological samples (e.g. crude plant extracts, and fungal broths). The sample or candidate compound may be in solid, emulsion, suspension, liquid, or gas form. Typically, the sample or candidate compound is processed (e.g., by the addition of a liquid buffer) so as to be a fluid (i.e., free flowing) form (e.g., emulsion, suspension, solution) in order to readily permit and simplify the detection and quantification of the LDL-proteoglycan binding in the compound's presence using the methods of the invention. Typically, the sample or candidate compound of interest is present in the sample composition at a concentration of $10^{-3}$ M (micromolar) or less, for example, often as low as $10^{-9}$ M (nanomolar), sometimes as low as $10^{-12}$ M (picomolar), and even as low as $10^{-13}$ M (sub-picomolar).

The "LDL" reagent used in the assay can be any reagent which comprises at least a fragment of apo-B100 protein and maintains the LDL-proteoglycan binding activity of at least 60% of wild-type levels, preferably at least 70%, more preferably at least 80%, still more preferably 90%, most preferably at essentially 100% of wild-type LDL-proteoglycan binding activity. The apo-B100 fragment is preferably complete and preferably a wild-type human apo-B100 protein, but mutant proteins which maintain proteoglycan binding activity can be employed. The LDL reagent can be an LDL expressed in a non-human animal or mammal like the recombinant control LDL described in Examples 3 and 4. Preferably the "LDL" reagent used in the assays is normal human plasma LDL obtained from human blood and purified as described in Example 4. The "LDL" used for the assay methods may optionally be labeled to facilitate detection or measurement of LDL-proteoglycan complex formed. The LDL may be labeled by any means known in the art including the incorporation of radionuclides (e.g. $^{125}$I, $^{35}$S, etc.) into the proteins or lipids of the LDL, inclusion of fluorescent lipid (e.g. diI), the attachment of enzymes (e.g. β-galactosidase, horseradish peroxidase, etc.), or the attachment of one of a pair of detectable binding partners (e.g. biotinylation).

The "proteoglycan" reagent used in the assay can be any proteoglycan which binds specifically to human LDL. Preferably proteoglycans isolated from the artery wall of an animal, mammal, or human, or isolated from arterial smooth muscle cells, preferably human, are used, including versican, perlecan, biglycan, or decorin. In addition, any commercially available preparation of proteoglycan or glucosaminoglycan can be used including chondroitin disaccharides, heparin, chondroitin sulfate A, chondroitin sulfate B, chondroitin sulfate C, heparin disaccharides, heparin-like substance sulodexide, or heparin-like substance mesoglycan. (Sigma) As with the LDL of the invention the "proteoglycan" reagent used in the assay methods may optionally be labeled to facilitate detection measurement of LDL-proteoglycan complex formed. The proteoglycan may be labeled by any means known in the art including the incorporation of radionuclides (e.g. $^{125}$I, $^{35}$S, etc.) into the proteins or disaccharides of the proteoglycan, the attachment of enzymes (e.g. β-galactosidase, horseradish peroxidase, etc.), or the attachment of one of a pair of detectable binding partners (e.g. biotinylation).

The assays of the invention involve mixing a proteoglycan reagent and an LDL reagent in the presence of a test compound, under conditions wherein the LDL binds to the proteoglycan to form an LDL-proteoglycan complex in the absence of said candidate compound. The appropriate conditions for such reaction mixtures are known in the art (See, e.g., Examples 8 and 10), and can in addition be determined empirically by observing whether LDL-proteoglycan complexes are formed. Protocols may utilize a solid support to separate unbound LDL and proteoglycan reagents from LDL-proteoglycan complex, or this separation may be performed by immunoprecipitation, separation by gel electrophoresis, or affinity chromatography.

In one preferred embodiment, the level of LDL-proteoglycan binding is determined by gel-mobility shift assay. Prior to the assay, radiolabeled proteoglycan preparations are dialyzed. Human plasma LDL and a candidate compound are incubated with approximately 2000 dpm of ($^{35}$S)biglycan or ($^{35}$S)versican for 1 h at 37° C. The samples are loaded into wells on agarose gel, and subjected to electrophoresis. Gels are then fixed, dried, and exposed to film. The ($^{35}$S)biglycan or ($^{35}$S)versican complexed to LDL appears as a band at the origin of the can be quantitatively evaluated. This procedure has the advantages that only microgram quantities of lipoproteins are required and the relative affinity of LDL binding to the proteoglycans can be determined at physiological ionic and pH conditions.

In a second preferred embodiment proteoglycan-LDL binding is measured in the presence of a candidate compound as a drug screening assay. A procedure for a competitive solid-phase plate assay is employed. Normal human plasma LDL (1.0 μg in 50 μl of phosphate-buffered saline (PBS) containing 0.01% EDTA per well) is immobilized by absorption to a solid support, preferably a polystyrene 96-well micrometer plates for 6 to 24 hours at 4° C. Excess LDL is removed by washing in PBS, and nonspecific sites on the plastic are blocked by incubation with PBS containing 5% bovine serum albumin (BSA) for 1 to 24 hours at 24° C. The wells are washed three times with PBS and then with binding buffer (10 mM Tris, 50 mM NaCl, 5 mM $CaCl_2$, 0.05% BSA). Biotinylated proteoglycans along with a candidate compound, preferably in micromolar quantities, are added to each well and incubated for approximately 1 hour at 24° C. The unbound proteoglycans are removed and the wells are washed for up to three times with 50 mM Tris, 90 mM NaCl, 5 mM $CaCl_2$, 0.05% BSA. Then 50 μl of streptavidin peroxidase (10 μg/ml) is added and incubated for approximately 2 hours at 24° C. The unbound streptavidin peroxidase is removed and the wells are washed three times with 50 mM Tris, 90 mM NaCl, 5 mM $CaCl_2$, 0.05% BSA. Finally a peroxidase substrate, preferably chromogen o-dianisidine, is added in an appropriate buffer and absorbency at 405 nm is measured. Negative control values are obtained by using normal human plasma LDL, or in its place recombinant LDL comprising wild-type human apo-B100, obtained as described above in Examples 1–4. When the proteoglycans are added no candidate compound is added to the negative control wells. Negative control values represent normal LDL proteoglycan binding. Positive control wells are obtained using the RK3359–3369SA LDL and the K3363E LDL obtained as described above in Examples 1–4 in place of the normal human plasma LDL. Again, when the proteoglycans are added no candidate compound added to the positive control wells. Positive control values represent defective LDL proteoglycan binding. Those candidate compounds which reduce LDL-proteoglycan binding are identified for further testing and possible use as lead compounds for pharmaceutical development and use.

In particularly preferred embodiments the assays of the invention are performed by robots which are able to add defined quantities of reagents to the well of a plate, as well as perform washes and incubation steps at various temperatures.

In another preferred embodiment candidate compounds which have been shown to affect, particularly inhibit, LDL-proteoglycan binding are tested to see if they also affect LDL/LDL receptor binding. This embodiment is particularly useful in drug screening assays in which compounds that disrupt LDL-proteoglycan binding with out affecting LDL/LDL receptor binding are sought as lead compounds as a part of the drug discovery process. In a particularly preferred embodiment mixtures of comprising LDL receptor, LDL, and a candidate compound that affects LDL-proteoglycan binding, are incubated under conditions wherein LDL binds to LDL receptor to form an LDL-LDL receptor complex in the absence of said inhibitor of LDL-proteoglycan binding. The difference between the amount of LDL-LDL receptor complex present in the mixture prepared with the candidate compound, and a control mixture prepared without the candidate compound are compared, and optionally any difference is correlated with said candidate compound's ability to affect LDL-LDL receptor binding activity.

Transgenic Animals In Vivo Model for Atherosclerosis

In addition, the present invention encompasses the use of transgenic non-human animals and mammals which express human apo-B100 as an in vivo model system for the study of atherosclerosis, and in vivo assay methods for identifying compounds which modulate atherosclerosis and/or LDL-proteoglycan binding. Identifying compounds which inhibit atherosclerosis or LDL-proteoglycan binding activity is the preferred use of this assay, but it can equally be used to identify compounds which result in an increase in atherosclerotic regions. Thus, the assays of the invention may be used to determine whether a particular food or drug composition tends to stimulate or inhibit the formation of atherosclerotic lesions. The in vivo assay of the invention generally involve administering a sample or candidate compound to the transgenic animal, measuring the extent of atherosclerosis or atherosclerotic lesions which results, and correlating the measured extent of atherosclerosis or atherosclerotic lesions with the candidate compound's ability to modulate atherosclerosis in vivo, typically by using a relationship determined from one or more control animals. In a preferred embodiment at least one of the control animals used expresses a proteoglycan$^-$receptor$^+$LDL.

In another preferred embodiment the transgenic non-human animals or mammals to which the candidate compounds or samples are administered, express a human apo-B100 protein in which the glutamine at amino acid position 2153 has been replaced with a leucine. This mutation abolishes the formation of apo-B48, resulting in a higher yield of recombinant apo-B100 LDL. Apo-B48 has distinct proteoglycan binding site(s) from Site B in apo-B100. Therefore use of this mutation in the in vivo assay methods of the invention provides an effective means for studying the portion of atherogenesis which is the result of apo-B100 mediated LDL-proteoglycan binding, as opposed to apo-B48 mediated chylomicron- and chylomicron remnant-proteoglycan binding.

In a qualitative assay, simply determining whether the measured atherosclerosis or atherosclerotic lesions is above or below a threshold value (established, for example, using recombinant LDL samples with known LDL-proteoglycan binding properties) may be sufficient to establish the assay result. Thus, unless otherwise required, the term "measuring" can refer to either qualitative or quantitative determination.

Typically, the sample or candidate compound described above for the assay for identifying agents affecting of LDL-proteoglycan binding is administered to the non-human mammal or animal, preferably a candidate compound which has demonstrated inhibition of LDL-proteoglycan binding in vitro is used. Preferably, the sample or candidate compound has previously been identified as a compound which affects or inhibits LDL-proteoglycan binding in one of the assays of the invention. The candidate compound can be administered by any means known in the art. Typically, the amount of sample or candidate compound of interest is controlled to deliver in a dose of $10^{-3}$ M (micromolar) or less, for example, often as low as $10^{-9}$ M (nanomolar), and sometimes as low as $10^{-12}$ M (picomolar) in the subject animal's plasma.

The animal used can be any non-human animal preferably a mammal, more preferably a primate, rabbit, pig, goat or rodent, still more preferably a mouse, most preferably the recombinant control mouse described in Example 3. The animal must express a human apo-B100 protein, or at least a sufficiently large fragment thereof to allow the animal's recombinant LDL to bind to endogenous arterial wall, which can be predicted by demonstrating LDL-proteoglycan binding in an in vitro assay (See, e.g., Example 8).

In addition, the non-human transgenic animal must be subjected to conditions wherein measurable atherosclerotic lesions form in the arteries of said animal. As used herein the phrase "conditions wherein measurable atherosclerotic lesions form in the arteries of said animal" is used to denote any conditions which are known to cause atherosclerotic lesions in the particular animal used in an experiment. These conditions are particular to the animal used and must be determined empirically to ensure that the lesions are in fact measurable by whatever method is used. Most of such conditions relate to the diet of the animal or to the animals genetic make up. With respect to diet, cholesterol, cholesteryl ester, bile salts and fats, particularly saturated fats are known to induce atherosclerotic lesions when consumed in high doses. The Paigen diet described in Example 9 is an example of such a dietary condition. In terms of genetics, factors such as defective LDL receptors, mutant apolipoprotein genes, particularly apo-B100, which disrupt LDL/LDL receptor binding are example of genetic conditions.

The amount of atherosclerosis or atherosclerotic lesions is measured by many methods known in the art including the morphometric imaging method described in Example 9, as well as arteriography and ultrasound. The difference between the extent of atherosclerosis or atherosclerotic lesions present in the animal which has been administered the test compound and a control animal which has not received the test compound is determined. Preferably the control animal is precisely the same type and strain of animal and that which received the candidate compound, and has been treated with the same conditions.

Mutant apo-B100 Proteins, Fragments and LDL:

The invention embodies polypeptides comprising a proteoglycan$^-$receptor$^+$Site B, and entire apo-B100 proteins comprising a proteoglycan$^{-receptor+}$Site B, as well as fragments thereof which comprise a proteoglycan$^-$receptor$^+$Site B flanked on at least one side by a contiguous sequence of at least N amino acids which is directly adjacent to Site B in the wild-type human apo-B100 sequence, where the number N is about 25 amino acids, preferably 20 amino acids, more preferably 15 amino acid, still more preferably 8 to 10 amino acids, most preferably 6 amino acids. The apo-B100 proteins of the invention also comprise proteins that have a leucine in place of glutamine at amino acid position 2153, which abolishes the formation of apo-B48, resulting in a higher yield of recombinant apo-B 100 LDL.

The proteins of the invention can be made using routine expression methods known in the art. The DNA encoding the desired polypeptide, may be ligated into an expression vector suitable for any convenient host. Both eukaryotic and prokaryotic host systems may be used in forming recombinant polypeptides, and a summary of some of the more common systems are included below in the description of expression vectors. The polypeptide is then isolated from lysed cells or from the culture medium and purified to the extent needed for its intended use. Purification may be by any technique known in the art, for example, differential extraction, salt fractionation, chromatography, centrifugation, and the like. See, for example, Methods in Enzymology for a variety of methods for purifying proteins.

In addition, shorter protein fragments may be produced by chemical synthesis. Alternatively the proteins of the invention may be extracted from recombinant LDL. Methods for purifying apolipoproteins, particularly apo-B100 are known in the art, and include the use of detergents or chaotropic agents to disrupt particles followed by differential extraction and separation of the apo-B100 proteins and lipids by ion exchange chromatography, affinity chromatography, sedimentation according to density, and gel electrophoresis. Recombinant LDL can be isolated from a transgenic animal as described in Examples 3 and 4. The term recombinant LDL also embraces reconstituted LDL as well as LDL derived from a transgenic non-human animal, as described above. Methods of reconstituting LDL are known in the art. See, for example, Corsini, A. et al. 1987. *J. Lipid Res.* 28:1410–1423. Such reconstituted LDL may comprise lipids from solely human sources, as well as lipids and labels which are not naturally associated with LDL. Such reconstituted recombinant LDL must, however, comprise a mutant human apo-B100 protein of the invention.

As used herein, the term "purified recombinant LDL" refers to a recombinant LDL which is essentially free, i.e., contains less than about 50%, preferably less than about 30%, and more preferably less than about 10%, even more preferably less than about 5%, and still more preferably less than about 1% of lipoproteins comprising one or more non-human apolipoproteins. Methods for purifying recombinant LDL include centrifugation to separate lipoproteins of a particular density from other plasma constituents, as well as affinity chromatography utilizing an antibody which is specific for an antigenic determinant found only on the recombinant LDL or only on the other lipoproteins produced by a transgenic non-human animal.

The present invention also encompasses non-LDL lipoprotein particles which comprise an apo-B100 protein or fragment of the invention. These lipoproteins may include other human apolipoproteins which are normally associated with apo-B100 (e.g. apo-E and possibly apo-C), and may have the same rough physical properties of VLDL or IDL. They may also include apo-lipoproteins which are native to the transgenic animal from which they are isolated. These non-LDL lipoproteins particles can be isolated and used as a source of purified mutant apo-B100 protein.

Antibodies to Proteoglycan⁻Receptor⁺Mutant apo-B100 Proteins and LDL:

Apo-B100 proteins comprising proteoglycan⁻receptor⁺ mutations, fragments thereof comprising Site B, and recombinant LDL particles comprising either of these apo-B100 proteins or fragments are used to produce antibodies, including both polyclonal and monoclonal. If polyclonal antibodies are desired, a suitable non-human animal, preferably a non-human mammal is selected, usually a mouse, rat, rabbit, goat, or horse, is immunized with an apo-B100 protein, fragment, or LDL comprising the proteoglycan⁻receptor⁺ Site B in the presence of an appropriate adjuvant (e.g. aluminum hydroxide, RIBI, etc.) which is known in the art. In addition the protein, fragment or LDL can be pretreated with an agent which will increase antigenicity, such agents are known in the art and include, for example, methylated bovine serum albumin (mBSA), bovine serum albumin (BSA), Hepatitis B surface antigen, and keyhole limpet hemocyanin (KLH). Serum from the immunized animal is collected, treated and tested according to known procedures. If the serum contains polyclonal antibodies to undesired epitopes, the polyclonal antibodies can be purified by immunoaffinity chromatography. Techniques for producing and processing polyclonal antisera are known in the art, see for example, Mayer and Walker (1987).

Alternatively, monoclonal antibodies directed against an apo-B100 protein, fragment, or LDL comprising the proteoglycan⁻receptor⁺Site B can also be readily produced by one of ordinary skill in the art. The general methodology for making monoclonal antibodies by hybridoma is well known. Immortal antibody-producing cell lines can be created by cell fusion. See, for example, Harlow, E., and D. Lane. 1988. Antibodies A Laboratory Manual. Cold Spring Harbor Laboratory. pp. 53–242.

Transgenic non-human animals or mammals which express a human apo-B100 LDL with a wild-type Site B amino acid sequence are particularly useful for preparing antibodies, as these animals will recognize all or most of the exposed regions of human apo-B100 as self antigens. Thus, when such an animal is exposed, for example, to an LDL particle comprising an apo-B100 with a proteoglycan⁻ receptor⁺Site B, this Site B will be one of the few if not the only new immunogenic site exposed, and antibodies to this mutant site will be preferentially produced. Alternatively, the antibodies of the invention can be screened by standard ELISA technique for there ability to bind to apo-B100 with a proteoglycan⁻receptor⁺Site B, while not binding to a recombinant control LDL.

Antibodies, both monoclonal and polyclonal, which are directed to a proteoglycan⁻receptor⁺Site B are useful for screening for the presence of such mutations in the population at large with standard RIA and ELISA assay techniques. In addition these antibodies are may be used to purify the a proteoglycan⁻receptor⁺recombinant LDL by affinity chromatography.

Polynucleotides, Cells, and Transgenic Animals:

The invention embodies polynucleotides which encode a polypeptide comprising a proteoglycan⁻receptor⁺Site B, and entire apo-B100 proteins comprising a proteoglycan⁻ receptor⁺Site B, as well as fragments thereof which comprise a proteoglycan⁻receptor⁺Site B flanked on at least one side by a contiguous sequence of at least N amino acids which is directly adjacent to Site B in the wild-type human apo-B100 sequence, where the number N is about 25 amino acids, preferably 20 amino acids, more preferably 15 amino acids, still more preferably 8 to 10 amino acids, most preferably 6 amino acids. Generally the polynucleotides of the invention comprise the naturally occurring nucleotide sequence for the portions of the gene which encode the amino acid sequences outside of Site B as shown in the apo-B100 gene sequence of Knott, T, et al. 1986. *Nature* 323:734–738. However, any naturally occurring silent codon variation or other silent codon variation can be employed to encode those amino acids outside of Site B. Similarly those nucleotide sequences which encode the portions of Site B which maintain the wild-type apo-B100 sequence will generally make use of the naturally occurring nucleotide sequence, but any naturally occurring silent codon variation or other silent codon variation can be employed. As for those amino acids which are changed or added to the proteoglycan⁻receptor⁺Site B, nucleic acid sequences generally will be chosen to optimize expression in the specific human or non-human animal in which the polynucleotide is intended to be used, making use of known codon preferences.

The nucleic acids of the invention include expression vectors, amplification vectors, PCR-suitable polynucleotides, and vectors which are suitable for the introduction of a polynucleotide of the invention into an embryonic stem cell for the production of transgenic non-human animals. In addition, vectors which are suitable for the introduction of a polynucleotide of the invention into cells, organs and individuals, including human individuals, for the purposes of gene therapy to reduce the severity of or prevent atherosclerosis are encompassed. The invention also encompasses targeting vectors and method for changing a wild-type Site B into a proteoglycan⁻receptor⁺Site B in a human apo-B100 gene contained within an embryonic stem cell.

The invention embodies amplification vectors, which comprise a polynucleotide of the invention, and an origin of replication. Preferably, such amplification vectors further comprise restriction endonuclease sites flanking the polynucleotide, so as to facilitate cleavage and purification of the polynucleotides from the remainder of the amplification vector, and a selectable marker, so as to facilitate amplification of the amplification vector. Most preferably, the restriction endonuclease sites in the amplification vector are situated such that cleavage at those site would result in no other amplification vector fragments of a similar size.

Thus, such an amplification vector may be transfected into a host cell compatible with the origin of replication of said amplification vector, wherein the host cell is a prokaryotic or eukaryotic cell, preferably a mammalian, insect, yeast, or bacterial cell, most preferably an *Escherichia coli* cell. The resulting transfected host cells may be grown by culture methods known in the art, preferably under selection compatible with the selectable marker (e.g., antibiotics). The amplification vectors can be isolated and purified by methods known in the art (e.g., standard plasmid prep procedures). The polynucleotide of the invention can be cleaved with restriction enzymes that specifically cleave at the restriction endonuclease sites flanking the polynucleotide, and the double-stranded polynucleotide fragment purified by techniques known in the art, including gel electrophoresis.

Alternatively linear polynucleotides comprising a polynucleotide of the invention may be amplified by PCR. The PCR method is well known in the art and described in, e.g., U.S. Pat. Nos. 4,683,195 and 4,683,202 and Saiki, R et al. 1988. *Science* 239:487–491, and European patent applications 86302298.4, 86302299.2 and 87300203.4, as well as *Methods in Enzymology* 1987 155:335–350.

The polynucleotides of the invention also include expression vectors. Expression vector systems, control sequences and compatible host are known in the art. For a review of these systems see, for example, U.S. Pat. No. 5,350,671, columns 45–48.

The polynucleotides of the invention can also be derivatized in various ways, including those appropriate for facilitating transfection and/or gene therapy. The polynucleotides can be derivatized by attaching a nuclear localization signal to it to improve targeted delivery to the nucleus. One well-characterized nuclear localization signal is the heptapeptide PKKKRKV (pro-lys-lys-lys-arg-lys-val) (SEQ ID NO:21). Preferably, in the case of polynucleotides in the form of a closed circle, the nuclear localization signal is attached via a modified loop nucleotide or spacer that forms a branching structure.

If it is to be used in vivo, the polynucleotide of the invention may be derivatized to include ligands and/or delivery vehicles which provide dispersion through the blood, targeting to specific cell types, or permit easier transit of cellular barriers. Thus, the polynucleotides of the invention may be linked or combined with any targeting or delivery agent known in the art, including but not limited to, cell penetration enhancers, lipofectin, liposomes, dendrimers, DNA intercalators, and nanoparticles. In particular, nanoparticles for use in the delivery of the polynucleotides of the invention are particles of less than about 50 nanometers diameter, nontoxic, non-antigenic, and comprised of albumin and surfactant, or iron as in the nanoparticle particle technology of SynGenix. In general the delivery vehicles used to target the polynucleotides of the invention may further comprise any cell specific or general targeting agents known in the art, and will have a specific trapping efficiency to the target cells or organs of from about 5 to about 35%.

The polynucleotides of the invention may be used ex vivo in a gene therapy method for obtaining cells or organs which produce proteoglycan⁻receptor⁺LDL. The cells are created by incubation of the target cell with one or more of the above-described polynucleotides under standard conditions for uptake of nucleic acids, including electroporation or lipofection. In practicing an ex vivo method of treating cells or organs, the concentration of polynucleotides of the invention in a solution prepare to treat target cells or organs is from about 0.1 to about 100 $\mu$M, preferably 0.5 to 50 $\mu$M, most preferably from 1 to 10 $\beta$M.

Alternatively, the oligonucleotides can be modified or co-administered for targeted delivery to the nucleus. Improved oligonucleotide stability is expected in the nucleus due to: (1) lower levels of DNases and RNases; and (2) higher oligonucleotide concentrations due to lower total volume.

Alternatively, the polynucleotides of the invention can be covalently bonded to biotin to form a biotin-polynucleotide prodrug by methods known in the art, and co-administered with a receptor ligand bound to avidin or receptor specific antibody bound to avidin, wherein the receptor is capable of causing uptake of the resulting polynucleotide-biotin-avidin complex into the cells. Receptors that cause uptake are known to those of skill in the art. Any transplantable cell type or organ can be used preferably hepatic cells, fetal hepatic cells or whole or partial livers.

The invention encompasses vectors which are suitable for the introduction of a polynucleotide of the invention into an embryonic stem cell for the production of transgenic non-human animals, which in turn result in the expression of recombinant LDL in the transgenic animal. The size of the apo-B100 dictates that a vector which can accommodate inserts which are tens of thousands of bases long. Yeast artificial chromosomes (YAC), bacterial artificial chromosomes (BAC), bacteriophage PI, and other vectors known in the art which are able to accommodate sufficiently large inserts to encode the entire apo-B100 gene. The 95-kb apo-B P1 plasmid p158 of Linton, M. et al. 1993. *J. Clin. Invest.* 92:3029–3037 makes a convenient vector system to use, as it already contains a full length apo-B100 gene.

Moreover, Borèn, J. et al. 1996. *Genome Res.* 6:1123–1130 have demonstrated how to isolate a 5.7 kb fragment of the apo-B100 gene which comprises Site B, in order to perform site-directed mutagenesis as described below in Examples 1 and 2, using RARE cleavage. In brief, RecA-assisted restriction endonuclease (RARE) cleavage consists of protecting a specific restriction endonuclease site with a complementary oligonucleotide. In the presence of RecA, a triplex DNA complex is formed that prevents methylation at the protected sites, for example EcoRI-35763 and EcoRI-41496 were protected by oligonucleotides (5'gaaaactcccacagcaagctaatgattatctgaattcattcaattgggagagacaa gtttcac 3') (SEQ ID NO:22) and (5'cacaagtgaaatatctggttaggatagaattctcccagttttcacaatgaaaacatc 3') (SEQ ID NO:23) respectively, while unprotected sites are methylated by the corresponding methylase. After dissociation of the oligonucleotides, the protected sites can be cleaved with the restriction endonuclease which corresponds to the protected sites, for example EcoRI. All of the non-protected EcoRI site had been methylated and were thus not subject to cleavage by the restriction enzyme. The resulting fragment of the apo-B100 gene can then be ligated into a smaller vector which is appropriate for site-directed mutagenesis, e.g. pZErO. The site-directed mutagenesis process is then conducted by techniques well known in the art, and the fragment is return and ligated to the larger vector from which it was cleaved. For site directed mutagenesis methods see, for example, Kunkel, T. 1985. *Proc. Natl. Acad. Sci. U.S.A.* 82:488; Bandeyar, M. et al. 1988. *Gene* 65: 129–133; Nelson, M., and M. McClelland 1992. *Methods Enzymol.* 216:279–303; Weiner, M. 1994. *Gene* 151: 119–123; Costa, G. and M. Weiner. 1994. *Nucleic Acids Res.* 22: 2423; Hu, G. 1993. *DNA and Cell Biology* 12:763–770; and Deng, W. and J. Nickoff. 1992. *Anal. Biochem.* 200:81.

Briefly, the transgenic technology used herein involves the inactivation, addition or replacement of a portion of a gene or an entire gene. For example the present technology includes the addition of human proteoglycan⁻receptor⁺apo-B100 genes with or without the inactivation of the non-human animal's native apolipoprotein genes, as described in the preceding two paragraphs and in the Examples. The invention also encompasses the use of vectors, and the vectors themselves which target and modify an existing human apo-B100 gene in a stem cell, whether it is contained in a non-human animal cell where it was previously introduced into the germ line by transgenic technology or it is a native apo-B100 gene in a human pluripotent cell. This transgene technology usually relies on homologous recombination in a pluripotent cell that is capable of differentiating into germ cell tissue. A DNA construct that encodes an altered region of comprising a proteoglycan⁻receptor⁺Site B or an altered region of the non-human animal's apolipoprotein gene the contains, for instance a stop codon to destroy expression, is introduced into the nuclei of embryonic stem cells. Preferably mice are used for this transgenic work. In a portion of the cells, the introduced DNA recombines with the endogenous copy of the cell's gene, replacing it with the altered copy. Cells containing the newly engineered genetic alteration are injected in a host embryo of the same species as the stem cell, and the embryo is reimplanted into a recipient female. Some of these embryos develop into chimeric individuals that posses germ cells entirely derived from the mutant cell line. Therefore, by breeding the chimeric progeny it is possible to obtain a new strain containing the introduced genetic alteration. See Capecchi 1989. *Science.* 244:1288–1292 for a review of this procedure.

The present invention encompasses the polynucleotides described herein, as well as the methods for making these polynucleotides including the method for creating a mutation in a proteoglycan⁻receptor⁺mutation in a human apo-B100 gene. In addition, the present invention encompasses cells which comprise the polynucleotides of the invention, including but not limited to amplification host cells comprising amplification vectors of the invention. Furthermore the present invention comprises the embryonic stem cells and transgenic non-human animals and mammals described herein which comprise a gene encoding a proteoglycan⁻receptor⁺human apo-B100 protein.

The invention also encompasses methods for preventing or reducing the severity of atherosclerosis in an animal or mammal, by expressing a polynucleotide encoding a proteoglycan⁻receptor⁺human apo-B100 protein or protein fragment of the invention. The polynucleotide encoding a proteoglycan⁻receptor⁺human apo-B100 protein or protein fragment of the invention is transduced into a cell, either ex vivo or in situ. In the case of ex vivo transduction, the transduced cell is then administered to an animal or mammal. Expression of the proteoglycan⁻receptor⁺human apo-B100 protein or protein fragment of the invention substantially prevents, ameliorates or reduces the severity of atherosclerosis in the animal or mammal.

The polynucleotide to be transduced is normally inserted into an appropriate expression vector, using standard molecular biology techniques. Appropriate expression vectors are easily selected by one of skill in the art, and generally include cis-acting transcription and translation nucleotide sequences which are operable in the cell to be transduced. Such elements are well known in the art, and include viral promoters and enhancers (e.g., the SV40 promoter and enhancer), mammalian constituitive promoters (e.g., the β-actin promoter), mammalian tissue-specific promoters and enhancers, polyadenylation signals, and the like. Preferably, an intron is introduced into the polynucleotide encoding the proteoglycan⁻receptor⁺human apo-B100 protein or protein fragment, as the presence of an intron frequently improves mRNA processing and export from the nucleus.

The expression vector may optionally include positive and negative selection markers. Positive selection markers are preferable when transduction is carried out ex vivo, because they permit enrichment of cells transduced with the polynucleotide. Positive selection markers are well known in the art, and include the neo$^r$ and hyg$^r$ genes, which confer resistance to gentamycin and hygromycin, respectively. A negative selection marker may be included to allow termination of expression of the proteoglycan⁻receptor⁺human apo-B100 protein or protein fragment, by killing of the transduced cells. One preferred negative selection marker is the herpes simplex virus 1 thymidine kinase (HSVtk) gene, which renders the transduced cells susceptible to ganciclovir. Alternately, fused positive/negative selection markers may be employed, such as the HyTK (hyg$^r$/HSVtk) fusion gene, which confers both hygromycin resistance and ganciclovir sensitivity.

The expression construct may be transduced into the target cell using any method known in the art, such as viral transduction, electroporation, lipid-mediated transduction, ballistic transduction, calcium phosphate transduction, or by naked DNA transfer, although viral transduction, lipid-mediated transduction and naked DNA transfer are preferred for in vivo transduction. In the case where viral transduction is employed, expression construct will also encode certain DNA or RNA virus proteins and/or signals, to allow packaging into infectious viral particles. The large size of the proteoglycan⁻receptor⁺human apo-B100 protein gene will constrain the selection of viral vectors for use in transducing target cells, as will be apparent to one of skill in the art, but most proteoglycan⁻receptor⁺human apo-B100 protein fragment constructs can be inserted into any viral vector known to be suitable for target cell transduction.

The quantity of cells transferred to the animal or mammal subject will depend on a variety of factors, including the severity of the subject's atherosclerosis (or risk for developing atherosclerosis), the expression levels of the transduced cells, the subject's medical history, and other factors known to those of skill in the art. In any case, an effective amount of transduced cells (i.e., an amount sufficient to prevent, ameliorate, or reduce atherosclerosis in the subject) are transferred to the subject.

Methods of ex vivo transduction are well known in the art. See, for example, U.S. Pat. No. 5,399,346. Viral transduction is also well known, and is disclosed in a number of issued U.S. patents, such as U.S. Pat. Nos. 5,672,344, 5,656,465, 5,139,941, and 5,851,529. Transduction of target cells with naked DNA technology is disclosed in, for example, U.S. Pat. No. 5,580,859. The quantity of the polynucleotide of the invention administered to the animal or mammal subject by in situ transduction will vary according to a number of parameters, such as the efficiency of the transduction method, the desired levels of expression, the subject's medical history, and other parameters known to one of skill in the art. In any case, an effective amount of a polynucleotide of the invention (i.e., an amount sufficient to prevent, ameliorate, or reduce atherosclerosis in the subject) is administered to the subject.

As will be apparent to one of skill in the art, blood levels of proteoglycan⁻receptor⁺human apo-B100 protein or protein fragment may be measured after in situ transduction or ex vivo transduction and transfer of transduced cells to the subject. If blood levels of the protein or protein fragment are not at desired levels, transduction or transduction and transfer may be repeated to achieve the desired levels of the protein or protein fragment of the invention.

After transduction (for in situ transduction) or transduction and transfer to the animal or mammal (for ex vivo transduction), expression of the polynucleotide encoding a proteoglycan⁻receptor⁺human apo-B100 protein or protein fragment results in prevention of or a reduction or amelioration of the severity of symptoms of atherosclerosis.

Throughout this application, various publications, patents, and published patent applications are cited. The disclosures of the publications, patents, and published patent specifications referenced in this application are hereby incorporated by reference into the present disclosure to more fully describe the state of the art to which this invention pertains.

EXAMPLES

Several of the methods of the present invention are described in the following examples, which are offered by way of illustration and not by way of limitation. Many other modifications and variations of the invention as herein set forth can be made without departing from the spirit and scope thereof and therefore only such limitations should be imposed as are indicated by the appended claims.

Example 1

Generation of Truncated P1 Plasmids and Isolation of DNA Fragments for Mutagenesis The 95-kb apo-B P1 plasmid p158 (Linton, M. et al. 1993. *J. Clin. Invest.* 92:3029–3037) was prepared and modified by RARE cleavage as described by Borèn, J. et al. 1996. *Genome Res.* 6:1123–1130. Oligomers EcoRI-35763 (5'gaaaactcccacagcaagctaatgattatctgaattcattcaattgggagagac aagtttcac 3') (SEQ ID NO:22) and EcoRI-41496 (5'cacaagtgaaatatctggttaggatagaattctcccagttttcacaatgaaaacatc 3') (SEQ ID NO:23) were used to make 5.7-kb-deleted P1 plasmid. A 5.7-kb fragment was isolated from the apo-B100 "Leu-Leu" plasmid with RARE cleavage using oligomers EcoRI-35763 and EcoRI-41496 and cloned into the pZErO-1 vector (Invitrogen). The apo-B100 "Leu-Leu" plasmid was used to increase the yield of apo-B100, since it contains a CAA to CTA mutation in codon 2153 that effectively abolished the formation of apo-B48. The latter of which is formed by an editing mechanism present in mouse livers (Yao, Z. et al. 1992. *J. Biol Chem.* 267:1175–1182).

Example 2

Site-Directed Mutagenesis of P1 DNA

The pZErO-5.7 kb plasmid was subjected to site-directed mutagenesis with the Morph System (5 Prime→3 Prime, Inc.®) using oligonucleotide K3363E (5'caagattgacaagagaaaggggattgaag 3') (SEQ ID NO:24) to mutate the lysine at reside 3363 to glutamic acid. The resulting plasmids were subjected to RARE cleavage with oligomers EcoRI-35763 and EcoRI-41496, and the mutated 5.7-kb fragment was isolated. After RARE cleavage of the 5.7-kb-deleted P1 plasmid with oligonucleotide EcoRI del. 5.7-kb (5'ggaaaactcccacagcaagctaatgattatctgaattctccc agttttcacaatgaaaacatc 3') (SEQ ID NO:25), the mutated 5.7-kb fragment was ligated into the linearized and phosphatased 5.7-kb-deleted P1 vector (Borèn, J. et al. 1996. *Genome Res.* 6:1123–1130).

Example 3

Human Apo-B Transgenic Mice

The transgenic mice were generated with a P1 bacteriophage clone (p158) (Linton, M. et al. 1993. *J. Clin. Invest.* 92:3029–3037) that spanned the human apo-B gene in which mutations had been introduced by RecA-assisted restriction endonuclease (RARE) cleavage (Borèn, J. et al. 1996. *Genome Res.* 6:1123–1130) as described in Examples 1 and 2.

P1 DNA was prepared and microinjected into fertilized mouse eggs (C57BL/6×SJL) (McCormick, S. et al. 1994. *Genet Anal Tech Appl* 11:158–164). Mice were housed in a pathogen-free barrier facility operating on a 12-h light/12-h dark cycle and were fed rodent chow containing 4.5% fat (Ralston Purina, St. Louis, Mo.).

Transgenic mice were identified at the time of weaning (21 days) by screening mouse plasma for human apo-B100 western dot-blot and western analysis with the monoclonal antibody 1D1 (Milne, R. et al. 1983. *Arteriosclerosis.* 3:23–30). Four different types of human recombinant LDL were generated (Table 1). The first of the transgenic mouse lines expressed recombinant control LDL. This LDL, however, had a leucine in place of glutamine at amino acid position 2153, which abolishes the formation of apo-B48, resulting in a higher yield of recombinant apo-B100 LDL. Its receptor-binding activity was found to be identical to that of LDL generated by the unmodified apo-B100 P1 bacteriophage clone. The second transgenic mouse line expressed a form of recombinant LDL that had a single amino acid mutation, the substitution of glutamine for the normally occurring arginine at residue 3500 in apo-B100 (R3500Q). We have also proven that this mutation is identical to the mutation that causes defective receptor binding in the genetic disorder familial defective apo-B100 (Borèn, J. et al. 1998. *J. Clin. Invest.* 101:1084–1093). Although it is outside the receptor-binding site (Site B), this mutation produces a conformational change that disrupts receptor binding. This is the only LDL that did not have the "Leu-Leu" mutation encoded in the apo-B mRNA. The third transgenic mouse line expressed a recombinant LDL in which the basic amino acids in Site B (residues 3359–3369) were converted to neutral amino acids. The arginine residues were converted to serines and the lysine residues to alanines (RK3359–3369SA). These changes virtually abolish the receptor-binding activity of the recombinant LDL; this finding along with other evidence demonstrated that Site B is the receptor-binding site of LDL (Borèn, J. et al. 1998. *J. Clin. Invesi.* 101: 1084–1093). The fourth transgenic mouse line expressed human recombinant LDL in which the lysine at residue 3363 of apo-B 100 was changed to glutamic acid (K3363E). This mutation was designed to disrupt proteoglycan binding if Site B plays a significant role in binding to proteoglycans.

TABLE 1

Mutants of the Human Apo-B Gene

| Recombinant LDL | LDL Receptor binding | Proteoglycan binding |
|---|---|---|
| Control LDL | Normal | Normal |
| R3500Q LDL | Defective | Normal |
| RK3359–3369SA LDL | Defective | Defective |
| K3363E LDL | Normal | Defective |

Example 4

Isolation of Recombinant Lipoproteins

Blood from mice fasted for 5 h was collected by cardiac puncture into tubes containing EDTA (final concentration 1 mg/ml), and the plasma was mixed with butylated hydroxytoluene (final concentration, 25 μM), phenylmethyl sulfonylfluoride (final concentration, 1 mM), and aprotinin (final concentration, 10 U/ml). The LDL (d=1.02–1.05 g/ml) were isolated by sequential ultracentrifugation (Ti 70 rotor) and dialyzed against 150 mM NaCl and 0.01% EDTA, pH 7.4, and the mouse apo-E and apo-B were removed by immunoaffinity chromatography. The d=1.02–1.05 g/ml fraction was mixed with an equal volume (850 μl) of AffiGel Hz (BioRad) and incubated for 17 hours at 4° C. in a gently rocking tube filled with nitrogen. The AffiGel Hz (100 g) had previously been coupled with mouse apo-E or mouse apo-B rabbit immunoglobulins from 50 ml of antiserum. Lipoproteins used for receptor-binding experiments were isolated and assayed within 1 week. Human plasma LDL, isolated from a single blood donor, were included as a control in each experiment.

The recombinant LDL were isolated from the human apo-B transgenic mouse plasma by ultracentrifugation, and the endogenous mouse apo-E- and apo-B-containing lipoproteins were removed by immunoaffinity chromatography. The purified lipoproteins were analyzed on western blots of 3–15% polyacrylamide-SDS gels with ECL western blotting detection reagents (Amersham). Purified recombinant LDL isolated from the plasma of the four lines of transgenic mice contained intact apo-B100 without any visible contamination (FIG. 1A). Western blot analysis showed that the recombinant LDL from all four transgenic mouse lines bound to the monoclonal antibody 1D1 (FIG. 1B), whose epitope is between amino acids 474 and 539 in human apo-B100 (Milne, R. et al. 1983. *Arteriosclerosis.* 3:23–30) and that only the unpurified recombinant LDL reacted with polyclonal antibodies against mouse apo-B and mouse apo-E (FIG. 1C and FIG. 1D, respectively), confirming that endogenous mouse apo-B and apo-E had been completely removed.

Example 5

Modification Of Recombinant LDL

To selectively modify arginines or lysines in apo-B100, recombinant LDL were incubated with acetic anhydride or cyclohexadione, respectively. Acetylation of LDL was carried out as described by Basu, S. et al. 1976. *Proc. Natl. Acad Sci. USA.* 73:3178–3182. In short, with continuous stirring in ice water bath, recombinant LDL (0.5 mg) in 1.0 ml 0.15 M NaCl and 0.01% EDTA were mixed with 1.5 μl saturated sodium acetate solution every 15 min over 1 hr. Cyclohexanedione modification of LDL was performed as by Mahley, R. et al. 1977. *J. Biol Chem.* 252:7279–7287. Recombinant LDL (0.5 mg) in 1 ml of 0.15 M NaCl and 0.01% EDTA was mixed with 2 ml of 0.15 M 1,2-cyclohexanedione in 0.2 M sodium borate buffer (pH 8.1) and incubated at 35° C. for 2 h. The sample was then dialyzed for 48 h against 0.15 M NaCl and 0.01% EDTA at 4° C.

Example 6

Cell Culture and Competitive Receptor Binding Assay

Human fibroblasts were cultured in Dulbecco's modified Eagle's medium (DMEM) containing 10% fetal bovine serum. Seven days before each experiment, the fibroblasts were plated into 12-well cell culture dishes (22-mm diameter per well) at ~12000 cells/well in the same medium. Two days before each experiment, the cells were transferred to DMEM containing 10% human lipoprotein-deficient serum. Normal human $^{125}$I-labeled LDL (2 μg/ml) along with increasing concentrations of unlabeled lipoproteins were added to the cells in DMEM containing 25 mM HEPES and 10% human lipoprotein-deficient serum. After a 3-h incubation at 4° C., the surface-bound radioactivity was determined. The amount of unlabeled lipoproteins needed to compete 50% with $^{125}$I-labeled LDL was determined from an exponential decay curve-fitting model (Arnold, K. et al. 1992. *Lipoprotein Analysis. A Practical Approach.* C. A. Converse, and E. R. Skinner, editors. Oxford University Press, Oxford. 145–168).

To evaluate the receptor-binding activity of the recombinant LDL, LDL from each transgenic line were tested with an in vitro competitive receptor-binding assay (FIG. 2). Recombinant LDL with the uncharged Site B (RK3359–3369SA) or with the R3500Q mutation had defective receptor binding ($ED_{50}$ >20 μg/ml for both), a finding in agreement with other results obtained in our lab (Borèn, J. et al. 1998. *J. Clin. Invest.* 101:1084–1093). The K3363E LDL had normal receptor binding equivalent to that of control LDL ($ED_{50}$ 2.4 and 2.3 μg/ml, respectively). Moreover, since LDL with the K3363E mutation retained LDL receptor-binding activity, these results also indicate that the mutation did not affect the overall folding and stability of the protein.

Example 7

Biglycan And Versican Isolation

Biglycan and versican were prepared from cultured human arterial smooth muscle cells metabolically labeled with ($^{35}$S)SO$_4$, as described previously (Chang, Y. et al. 1983. *J. Biol. Chem.* 258:5679–5688). Briefly, cell medium was concentrated on DEAE-Sephacel minicolumns equilibrated in 8 M urea, 0.25 M NaCl, and 0.5% CHAPS. The ($^{35}$S)labeled proteoglycans were eluted with 8 M urea, 3 M NaCl, and 0.5% CHAPS and applied to a Sepharose CL-2B column equilibrated in 8 M urea and 0.5% CHAPS. Small aliquots of the resulting fractions were counted to provide a profile of the separated material. The fractions were then combined into four pools: pool 1, $K_{av}$=0.2; pool 2, $K_{av}$=0.2–0.4; pool 3, $K_{av}$=0.4–0.55; and pool 4; $K_{av}$=0.55–0.8. Eluted material in each pool was concentrated on Centricon-50 spin columns and dialyzed into Buffer A used for binding assays. The bulk of the ($^{35}$S)SO$_4$ radioactivity was present in pools 1 and 3. Western blot analyses showed that pool 1 contained versican and was negative for perlecan, biglycan, and decorin. Pool 3 contained only biglycan and no immunoreactivity for perlecan, versican, or decorin. Only very small amounts of decorin were found in pool 4.

Example 8

Gel-Mobility Shift Assay

The interaction between LDL and biglycan or versican was investigated by a gel-mobility shift assay (Camejo, G. et al. 1993. *J. Biol Chem.* 268:14131–14137). Before the assay, the ($^{35}$S)biglycan and ($^{35}$S)versican preparations were dialyzed extensively at 4° C. against 10 mM HEPES, 150 mM NaCl, 5 mM CaCl$_2$, and 2 mM MgCl$_2$ (pH 7.4, Buffer A), and the protein concentrations were determined (BioRad Laboratories) with bovine gamma globulin as the standard. Increasing concentrations of LDL were incubated with approximately 2000 dpm of($^{35}$S)biglycan or ($^{35}$S)versican for 1 h at 37° C. in a total volume of 20 μl of Buffer A. Three microliters of bromophenol blue:glycerol (1:1, v/v) was added to the samples, and 20 μl was loaded into wells of 0.7% NuSieve (FMC BioProducts) agarose gels prepared on Gel-Bond film (FMC BioProducts). Electrophoresis was run for 3 h at 60V with recirculating buffer (10 mM HEPES, 2 mM CaCl$_2$, 4 mM MgCl$_2$ pH 7.2) in a cold room. Gels were fixed with 0.1% cetyl pyridium chloride in 70% ethanol for 90 min, air-dried, and exposed to Hyper Film-MP (Amersham Life Sciences) at −70° C. The ($^{35}$S)biglycan or ($^{35}$S)versican complexed to LDL appears as a band at the origin of the were quantitatively evaluated with a Hewlett Packard Scan Jet II cx and ImageQuant software (Molecular Dynamics).

Gel-shift Analysis of Recombinant LDL with Versican and Biglycan

Figure 3B:
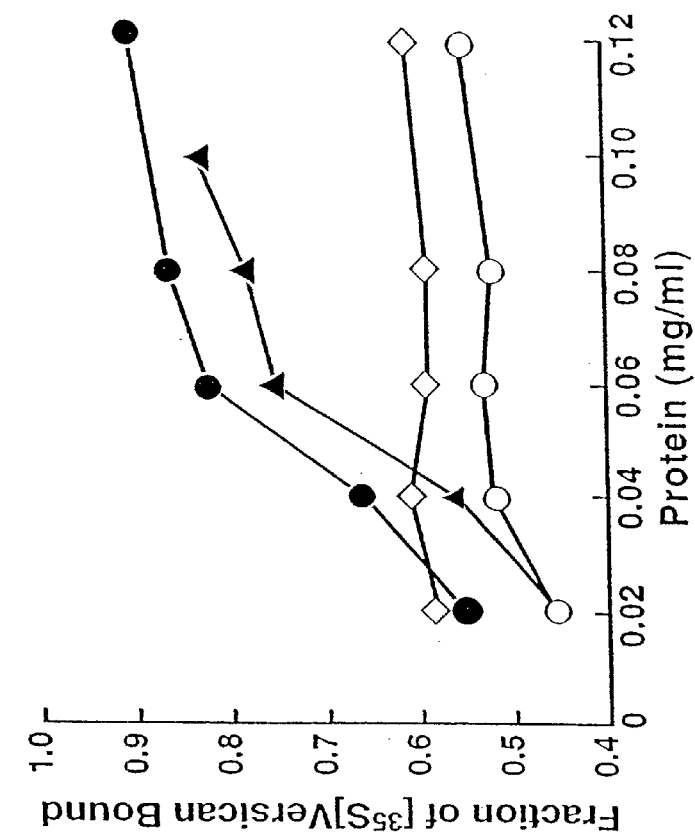
FIG. 3 is a graph of a gel-shift analysis of mouse-derived recombinant LDL with ($^{35}$S)biglycan and ($^{35}$S)versican. The abilities of recombinant control LDL (closed triangle), R3500Q LDL (closed square), RK3359–3369SA LDL (open diamond), and K3363E LDL (open circle) to interact with ($^{35}$S)biglycan (FIG. 3A) and ($^{35}$S)versican (FIG. 3B) were determined. The recombinant lipoproteins were isolated from 15 mice, and endogenous apo-E and apo-B were removed by immunoaffinity chromatography. The results represent the average data from three independent experiments performed with freshly isolated LDL for each experiment. Human plasma LDL (closed circle) was included as a control.
Figure 3A:
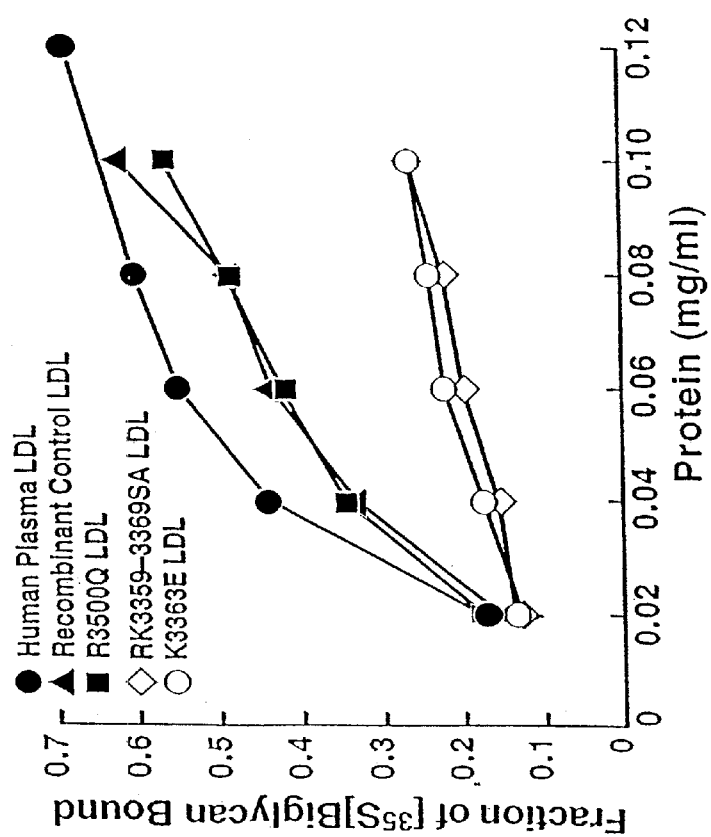

To determine the ability of the different recombinant LDL to interact with proteoglycans, recombinant control, R3500Q, RK3359–3369SA, and K3363E LDL were isolated and subjected to gel-shift analysis (Camejo, G. et al. 1993. *J. Biol Chem.* 268:14131–14137). This procedure has the advantages that only microgram quantities of lipoproteins are required and the relative affinity of LDL binding to the proteoglycans can be determined at physiological ionic and pH conditions. In three independent experiments, recombinant control LDL and R3500Q LDL bound ($^{35}$S)versican and ($^{35}$S)biglycan almost as efficiently as human plasma LDL, but recombinant RK3359–3369SA and K3363E LDL had severely impaired binding to both ($^{35}$S)versican and ($^{35}$S)biglycan (FIG. 3). Thus, mutations of basic amino acids in Site B dramatically reduced the ability of apo-B100 to interact with proteoglycans. Of particular interest was that recombinant K3363E LDL interacted defectively with both versican and biglycan but had normal receptor binding. Recombinant control LDL with and without the "Leu-Leu" mutation displayed identical binding to ($^{35}$S)versican and ($^{35}$S)biglycan (data not shown). Thus, this mutation does not affect the binding of LDL to proteoglycans.

Gel-shift Analysis of Acetylated or Cyclohexanedione-modified Recombinant LDL

Figure 4B:
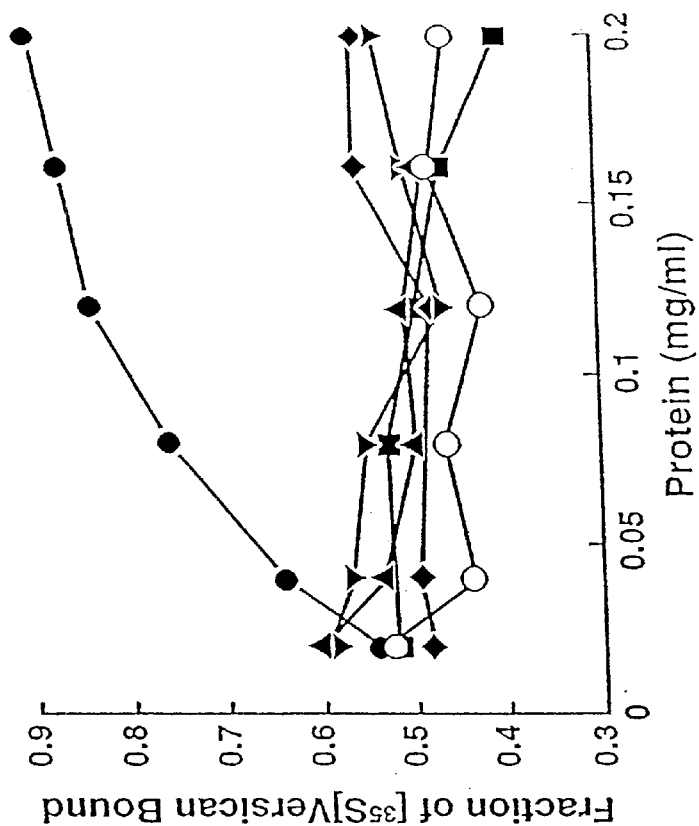
FIG. 4 is a graph of a gel-shift analysis of mouse-derived recombinant LDL with ($^{35}$S)versican and ($^{35}$S)biglycan after selective modification. The abilities of recombinant control LDL (closed circle) and RK3359–3369SA LDL (closed diamond), cyclohexanedione-modified control LDL (closed triangle, point down) and RK3359–3369SA LDL(closed triangle, point up), and acetylated control LDL (open circle) and RK3359–3369SA LDL (closed square) to interact with ($^{35}$S)versican (FIG. 4A)or ($^{35}$S)biglycan (FIG. 4B) were determined. The recombinant lipoproteins were isolated from 15 mice, and endogenous apo-E and apo-B were removed by immunoaffinity chromatography. The isolated recombinant LDL were treated with (FIG. 4A) acetic anhydride or (FIG. 4B) cyclohexanedione to selectively modify all arginines or lysines, respectively, in apo-B100.
Figure 4A:
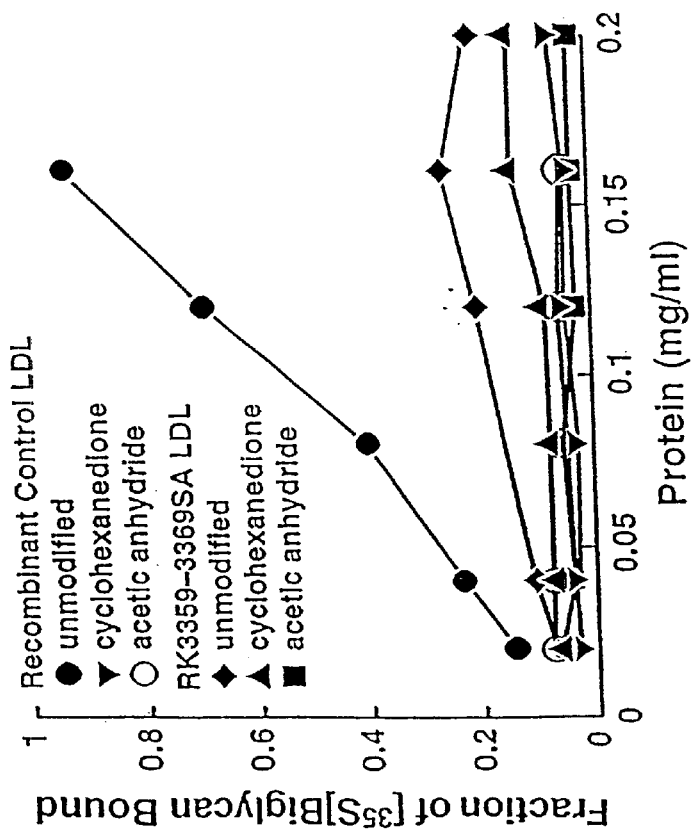

Mutagenesis of Site B severely reduced its interaction with versican and biglycan. To test the importance of the remaining clusters of basic amino acids for the interaction of LDL with versican or biglycan, the remaining arginines or lysines in apo-B100 were selectively modified to abolish the receptor-binding and heparin-binding activities of LDL. Recombinant LDL isolated from human apo-B transgenic mice expressing recombinant control or RK3359–3369SA LDL were divided into three aliquots. Two aliquots were selectively modified with acetic anhydride or cyclohexanedione to change the arginines and lysines, respectively. The ability of the modified recombinant control or RK3359–3369SA LDL to bind ($^{35}$S)biglycan or ($^{35}$S)versican was compared with that of unmodified recombinant LDL by gel-shift analysis. Again, unmodified RK3359–3369SA LDL had greatly reduced ability to interact with ($^{35}$S)biglycan or ($^{35}$S)versican (FIG. 4). Furthermore, the unmodified RK3359–3369SA LDL bound proteoglycans almost identically before and after chemical modification; only a minor difference was detected in the ($^{35}$S)biglycan gel-shift assay (FIG. 4A). These data demonstrate that Site B is the most important functional site for interaction with proteoglycans and that the seven other potential sites do not play a significant role.

Example 9

Initial In Vivo Atherosclerosis Studies Using Proteoglycan-Binding-Defective LDL These studies were designed to determine if elevated levels of proteoglycan-binding-defective LDL would be less atherogenic than similar levels of wild-type recombinant LDL. The RK3359–3369SA construct was used to generate mice expressing the proteoglycan-binding-defective LDL. The apo-B transgenic mice used in this atherosclerosis study were hybrids of the genetic strains C57BL/6 (50%) and SJL (50%). Non-transgenic mice with the same genetic background were also included in the study. The transgenic mice were fed a Paigen diet containing 1.2% cholesterol, 0.5% bile salts, and 20% fat for 17 weeks. The mice were then sacrificed, and the aortas were perfusion fixed and analyzed with the en face procedure, in which the entire aorta is pinned out flat, stained with Sudan IV, and analyzed with a morphometric image-analysis system (Image-1/AT) to quantitate the extent of atherosclerosis.

Figure 5:
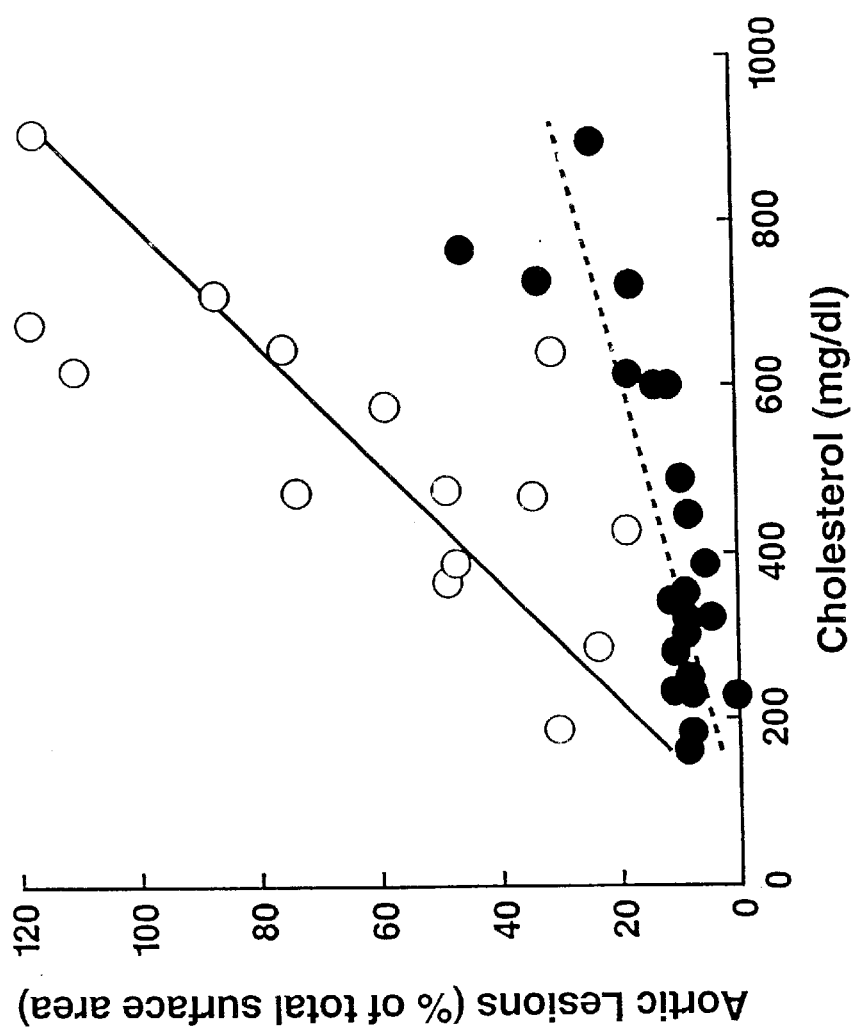
FIG. 5 is a graph demonstrating the correlation between the percentage of total aortic surface area covered by lesions and the plasma cholesterol levels of transgenic mice expressing either normal human recombinant LDL (open circle) or defective-proteoglycan-binding LDL (closed circle) after the mice had been fed a high-fat, high-cholesterol diet for 17 weeks.
Figure 6:
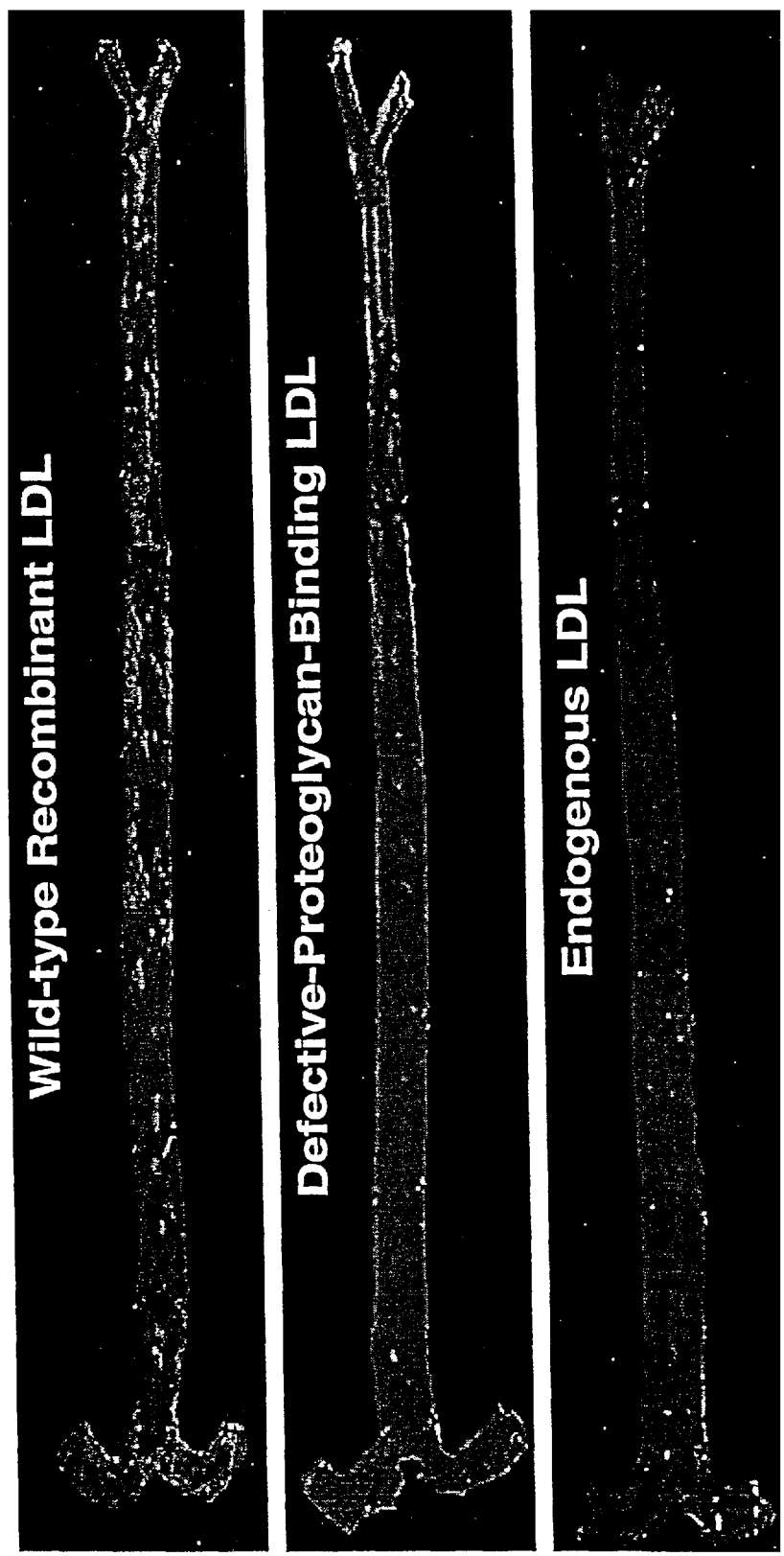
FIG. 6 is a half-tone reproduction of photographs of Sudan IV-stained aorta from a mouse expressing human wild-type recombinant LDL (top), proteoglycan-binding-defective LDL (center), and endogenous LDL (bottom).

In both groups of transgenic mice, the percentage of the vessel wall covered by atherosclerotic lesions correlated with the plasma cholesterol level (FIG. 5). However, the extent of atherosclerosis differed dramatically between the groups. The transgenic mice expressing the RK3359–3369SA LDL had strikingly less atherosclerosis than mice expressing the wild-type recombinant LDL. It should be emphasized that the only difference between these two groups of transgenic mice is the mutation of the apo-B gene in the one group that prevents the binding of LDL to proteoglycans and to the LDL receptor. Representative aortas from a single wild-type recombinant LDL mouse, an RK3359–3369SA LDL mouse, and a non-transgenic mouse are shown in FIG. 6. The non-transgenic mouse had essentially no atherosclerosis, a finding that was consistent with the analysis of nine other non-transgenic mice that had been on a high-fat, high-cholesterol diet for 17 weeks.

Example 10

Proteoglycan-LDL Binding Drug Screening Assay

A procedure for a competitive solid-phase plate assay is employed (Edwards, I. et al. 1993. *J. Lipid Res.*

34:1155–1163; and Steele, R. et al. 1987. *Atherosclerosis.* 65:51–62). Normal human plasma LDL (1.0 µg in 50 µl of phosphate-buffered saline (PBS) containing 0.01% EDTA per well) is immobilized by absorption to polystyrene 96-well micrometer plates for 18 hours at 4° C. Excess LDL is removed by washing in PBS, and nonspecific sites on the plastic are blocked by incubation with PBS containing 5% bovine serum albumin (BSA) for 2 hours at 24° C. The wells are washed three times with PBS and then with binding buffer (10 mM Tris, 50 mM NaCl, 5 mM $CaCl_2$, 0.05% BSA). Biotinylated proteoglycans along with a candidate compound are added to each well and incubated for 1 hour at 24° C. The unbound proteoglycans are removed and the wells are washed three times with 50 mM Tris, 90 mM NaCl, 5 mM $CaCl_2$, 0.05% BSA before 50 µl of streptavidin peroxidase (10 µg/ml) is added and incubated for 2 hours at 24° C. The unbound streptavidin peroxidase is removed and the wells are washed three times with 50 mM Tris, 90 mM NaCl, 5 mM $CaCl_2$, 0.05% BSA. Finally the peroxidase substrate, chromogen o-dianisidine, is added and absorbency at 405 nm is measured.

Negative control values are obtained by using normal human plasma LDL, or in its place recombinant LDL comprising wild-type human apo-B100, obtained as described above in Examples 1–4. When the proteoglycans are added no candidate compound is added to the negative control wells. Negative control values represent normal LDL proteoglycan binding.

Positive control wells are obtained using the RK3359–3369SA LDL and the K3363E LDL obtained as described above in Examples 1–4 in place of the normal human plasma LDL. Again, when the proteoglycans are added no candidate compound added to the positive control wells. Positive control values represent defective LDL proteoglycan binding.

Those candidate compounds which reduce LDL-proteoglyean binding are identified for further testing and possible use as lead compounds for pharmaceutical development and use.

Example 11

Drug Screening Receptor Binding Assay

Those candidate compounds which demonstrate disruption of LDL-proteoglycan binding in Example 10 or other LDL-proteoglycan binding assays are tested to ensure that they do not disrupt LDL receptor binding.

Human fibroblasts are cultured in Dulbecco's modified Eagle's medium (DMEM) containing 10% fetal bovine serum. Seven days before each experiment, the fibroblasts are plated into 12-well cell culture dishes (22-mm diameter per well) at ~12000 cells/well in the same medium. Two days before each experiment, the cells are transferred to DMEM containing 10% human lipoprotein-deficient serum. Normal human $^{125}$I-labeled LDL (2 µg/ml) along with a candidate compound which has been shown to disrupt LDL proteoglycan binding is added to each well in DMEM containing 25 mM HEPES and 10% human lipoprotein-deficient serum. After a 3-h incubation at 4° C., the medium is removed, and washed three times with DMEM containing 25 mM HEPES and 10% human lipoprotein-deficient serum. The surface-bound radioactivity is determined for each well.

Example 12

Use of apo-B transgenic Mice as In Vivo Atherosclerosis Model System for Determining the Efficacy of Candidate Compounds The transgenic mice described above in Examples 1–3 are used to test the efficacy of candidate compounds at reducing atherosclerosis. Transgenic mice expressing the wild-type human apo-B100 are each administered a candidate compound for 17 weeks, and fed a Paigen diet containing 1.2% cholesterol, 0.5% bile salts, and 20% fat during this period. The mice are then sacrificed, and the aortas are perfusion fixed and analyzed with the en face procedure, in which the entire aorta is pinned out flat, stained with Sudan IV, and analyzed with a morphometric image-analysis system (Image-1/AT) to quantitate the extent of atherosclerosis.

Negative control values are obtained using transgenic mice with the wild-type human apo-B100 which are not administered a candidate compound but are fed the Paigen diet. Positive control values are obtained using transgenic mice expressing the RK3359–3369SA apo-B100 and the K3363E LDL apo-B100, which can be obtained as described in Examples 1–3 above, which are fed the Paigen diet for 17 weeks.

What is claimed is:

1. A method for determining whether a compound affects LDL binding to proteoglycan and does not substantially affect LDL binding to LDL receptor, the method comprising:
    a) comparing the level of LDL binding to proteoglycan in the presence of the compound with the level of LDL binding to proteoglycan in the absence of the compound;
    b) comparing the level of LDL binding to LDL receptor in the presence of the compound with the level of LDL binding to LDL receptor in the absence of the compound;
        wherein the levels of binding in step (a) were determined by incubating mixtures comprising proteoglycan and LDL in the presence or absence of the compound under conditions where LDL binds to proteoglycan in the absence of the compound; and
        wherein the levels of binding in step (b) were determined by incubating mixtures comprising LDL and LDL receptor in the presence or absence of the compound under conditions where LDL binds to LDL receptor in the absence of the compound; and
    c) correlating any difference in the levels of binding in step (a) with the compound's ability to affect LDL-proteoglycan binding activity, and
    correlating any difference in the levels of binding in step (o) with the compound's ability to affect LDL-LDL receptor binding activity.

2. The method according to claim 1, wherein the LDL of the mixtures used to determine the levels of binding in step (a) was attached to a solid support.

3. The method according to claim 2, wherein the proteoglycan of the mixtures used to determine the levels of binding in step (a) was labeled.

4. The method according to claim 3, wherein the label is biotin.

5. The method according to claim 4, wherein the levels of binding in step (a) were determined further comprising the steps of:

contacting the solid support after the preparation of the mixtures of step (a) with streptavidin peroxidase under conditions wherein biotin binds to streptavidin to form a biotin-streptavidin complex;

detecting any enzyme activity of the peroxidase bound to the solid support.

* * * * *

UNITED STATES PATENT AND TRADEMARK OFFICE
CERTIFICATE OF CORRECTION

PATENT NO. : 6,579,682 B1
APPLICATION NO. : 09/265222
DATED : June 17, 2003
INVENTOR(S) : Thomas Innerarity et al.

Page 1 of 1

It is certified that error appears in the above-identified patent and that said Letters Patent is hereby corrected as shown below:

Col. 1, line 11

Please replace the STATEMENT OF RIGHTS TO INVENTIONS MADE UNDER FEDERALLY SPONSORED RESEARCH with the following:

STATEMENT OF RIGHTS TO INVENTIONS MADE UNDER FEDERALLY SPONSORED RESEARCH

"This invention was funded in part by National Institutes of Health program project grant HL41633. The U.S. Government may have certain rights to this invention." to read:

STATEMENT OF RIGHTS TO INVENTIONS MADE UNDER FEDERALLY SPONSORED RESEARCH

-- This invention was funded in part by National Institutes of Health program project grant HL41633. The U.S. Government has certain rights in the invention. --

Signed and Sealed this

Twenty-second Day of December, 2009

David J. Kappos
*Director of the United States Patent and Trademark Office*

SEQUENCE LISTING

<160> NUMBER OF SEQ ID NOS: 25

<210> SEQ ID NO 1
<211> LENGTH: 10
<212> TYPE: PRT
<213> ORGANISM: Homo sapiens
<220> FEATURE:
<221> NAME/KEY: MUTAGEN
<222> LOCATION: 6
<223> OTHER INFORMATION: Missense mutation

<400> SEQUENCE: 1

Thr Arg Leu Thr Arg Glu Arg Gly Leu Lys
 1               5                  10

```
<210> SEQ ID NO 2
<211> LENGTH: 10
<212> TYPE: PRT
<213> ORGANISM: Homo sapiens
<220> FEATURE:
<221> NAME/KEY: MUTAGEN
<222> LOCATION: 6
<223> OTHER INFORMATION: Missense mutation

<400> SEQUENCE: 2

Thr Arg Leu Thr Arg Asp Arg Gly Leu Lys
 1               5                  10

<210> SEQ ID NO 3
<211> LENGTH: 10
<212> TYPE: PRT
<213> ORGANISM: Homo sapiens
<220> FEATURE:
<221> NAME/KEY: MUTAGEN
<222> LOCATION: 6
<223> OTHER INFORMATION: Missense mutation

<400> SEQUENCE: 3

Thr Arg Leu Thr Arg Ala Arg Gly Leu Lys
 1               5                  10

<210> SEQ ID NO 4
<211> LENGTH: 10
<212> TYPE: PRT
<213> ORGANISM: Homo sapiens
<220> FEATURE:
<221> NAME/KEY: MUTAGEN
<222> LOCATION: 6
<223> OTHER INFORMATION: Missense mutation

<400> SEQUENCE: 4

Thr Arg Leu Thr Arg Thr Arg Gly Leu Lys
 1               5                  10

<210> SEQ ID NO 5
<211> LENGTH: 10
<212> TYPE: PRT
<213> ORGANISM: Homo sapiens
<220> FEATURE:
<221> NAME/KEY: MUTAGEN
<222> LOCATION: 6
<223> OTHER INFORMATION: Missense mutation

<400> SEQUENCE: 5

Thr Arg Leu Thr Arg Ser Arg Gly Leu Lys
 1               5                  10

<210> SEQ ID NO 6
<211> LENGTH: 10
<212> TYPE: PRT
<213> ORGANISM: Homo sapiens
<220> FEATURE:
<221> NAME/KEY: MUTAGEN
<222> LOCATION: 6
<223> OTHER INFORMATION: Missense mutation

<400> SEQUENCE: 6

Thr Arg Leu Thr Arg Gln Arg Gly Leu Lys
 1               5                  10

<210> SEQ ID NO 7
<211> LENGTH: 10
<212> TYPE: PRT
<213> ORGANISM: Homo sapiens
```

```
<220> FEATURE:
<221> NAME/KEY: MUTAGEN
<222> LOCATION: 5
<223> OTHER INFORMATION: Missense mutation

<400> SEQUENCE: 7

Thr Arg Leu Thr Glu Lys Arg Gly Leu Lys
 1               5                  10

<210> SEQ ID NO 8
<211> LENGTH: 10
<212> TYPE: PRT
<213> ORGANISM: Homo sapiens
<220> FEATURE:
<221> NAME/KEY: MUTAGEN
<222> LOCATION: 5
<223> OTHER INFORMATION: Missense mutation

<400> SEQUENCE: 8

Thr Arg Leu Thr Asp Lys Arg Gly Leu Lys
 1               5                  10

<210> SEQ ID NO 9
<211> LENGTH: 10
<212> TYPE: PRT
<213> ORGANISM: Homo sapiens
<220> FEATURE:
<221> NAME/KEY: MUTAGEN
<222> LOCATION: 7
<223> OTHER INFORMATION: Missense mutation

<400> SEQUENCE: 9

Thr Arg Leu Thr Arg Lys Glu Gly Leu Lys
 1               5                  10

<210> SEQ ID NO 10
<211> LENGTH: 10
<212> TYPE: PRT
<213> ORGANISM: Homo sapiens
<220> FEATURE:
<221> NAME/KEY: MUTAGEN
<222> LOCATION: 7
<223> OTHER INFORMATION: Missense mutation

<400> SEQUENCE: 10

Thr Arg Leu Thr Arg Lys Asp Gly Leu Lys
 1               5                  10

<210> SEQ ID NO 11
<211> LENGTH: 10
<212> TYPE: PRT
<213> ORGANISM: Homo sapiens
<220> FEATURE:
<221> NAME/KEY: MUTAGEN
<222> LOCATION: 2
<223> OTHER INFORMATION: Missense mutation

<400> SEQUENCE: 11

Thr Glu Leu Thr Arg Lys Arg Gly Leu Lys
 1               5                  10

<210> SEQ ID NO 12
<211> LENGTH: 10
<212> TYPE: PRT
<213> ORGANISM: Homo sapiens
<220> FEATURE:
<221> NAME/KEY: MUTAGEN
<222> LOCATION: 2
<223> OTHER INFORMATION: Missense mutation
```

```
<400> SEQUENCE: 12

Thr Asp Leu Thr Arg Lys Arg Gly Leu Lys
1               5                   10

<210> SEQ ID NO 13
<211> LENGTH: 9
<212> TYPE: PRT
<213> ORGANISM: Homo sapiens
<220> FEATURE:
<221> NAME/KEY: MUTAGEN
<222> LOCATION: (5)...(6)
<223> OTHER INFORMATION: Single amino acid deletion between residues 5
      and 6

<400> SEQUENCE: 13

Thr Arg Leu Thr Arg Arg Gly Leu Lys
1               5

<210> SEQ ID NO 14
<211> LENGTH: 9
<212> TYPE: PRT
<213> ORGANISM: Homo sapiens
<220> FEATURE:
<221> NAME/KEY: MUTAGEN
<222> LOCATION: (4)...(5)
<223> OTHER INFORMATION: Single amino acid deletion between residues 4
      and 5

<400> SEQUENCE: 14

Thr Arg Leu Thr Lys Arg Gly Leu Lys
1               5

<210> SEQ ID NO 15
<211> LENGTH: 9
<212> TYPE: PRT
<213> ORGANISM: Homo sapiens
<220> FEATURE:
<221> NAME/KEY: MUTAGEN
<222> LOCATION: (6)...(7)
<223> OTHER INFORMATION: Single amino acid deletion between residues 6
      and 7

<400> SEQUENCE: 15

Thr Arg Leu Thr Arg Lys Gly Leu Lys
1               5

<210> SEQ ID NO 16
<211> LENGTH: 11
<212> TYPE: PRT
<213> ORGANISM: Homo sapiens
<220> FEATURE:
<221> NAME/KEY: MUTAGEN
<222> LOCATION: 6
<223> OTHER INFORMATION: Insertion of a single amino acid

<400> SEQUENCE: 16

Thr Arg Leu Thr Arg Glu Lys Arg Gly Leu Lys
1               5                   10

<210> SEQ ID NO 17
<211> LENGTH: 11
<212> TYPE: PRT
<213> ORGANISM: Homo sapiens
<220> FEATURE:
<221> NAME/KEY: MUTAGEN
<222> LOCATION: 7
<223> OTHER INFORMATION: Insertion of a single amino acid
```

```
<400> SEQUENCE: 17

Thr Arg Leu Thr Arg Lys Glu Arg Gly Leu Lys
1               5                   10

<210> SEQ ID NO 18
<211> LENGTH: 11
<212> TYPE: PRT
<213> ORGANISM: Homo sapiens
<220> FEATURE:
<221> NAME/KEY: MUTAGEN
<222> LOCATION: 6
<223> OTHER INFORMATION: Insertion of a single amino acid

<400> SEQUENCE: 18

Thr Arg Leu Thr Arg Asp Lys Arg Gly Leu Lys
1               5                   10

<210> SEQ ID NO 19
<211> LENGTH: 11
<212> TYPE: PRT
<213> ORGANISM: Homo sapiens
<220> FEATURE:
<221> NAME/KEY: MUTAGEN
<222> LOCATION: 7
<223> OTHER INFORMATION: Insertion of a single amino acid

<400> SEQUENCE: 19

Thr Arg Leu Thr Arg Lys Asp Arg Gly Leu Lys
1               5                   10

<210> SEQ ID NO 20
<211> LENGTH: 10
<212> TYPE: PRT
<213> ORGANISM: Homo sapiens
<220> FEATURE:
<221> NAME/KEY: BINDING
<222> LOCATION: (1)...(10)
<223> OTHER INFORMATION: Putative proteoglycan binding site of wild-type
      human apo-B100 protein

<400> SEQUENCE: 20

Thr Arg Leu Thr Arg Lys Arg Gly Leu Lys
1               5                   10

<210> SEQ ID NO 21
<211> LENGTH: 7
<212> TYPE: PRT
<213> ORGANISM: Artificial Sequence
<220> FEATURE:
<221> NAME/KEY: SIGNAL
<222> LOCATION: (1)...(7)
<223> OTHER INFORMATION: Nuclear localization signal from the simian
      virus 40 large-T antigen
<220> FEATURE:
<221> NAME/KEY: PEPTIDE
<222> LOCATION: (1)...(7)
<223> OTHER INFORMATION: Synthetic Construct

<400> SEQUENCE: 21

Pro Lys Lys Lys Arg Lys Val
1               5

<210> SEQ ID NO 22
<211> LENGTH: 63
<212> TYPE: DNA
<213> ORGANISM: Artificial Sequence
<220> FEATURE:
<223> OTHER INFORMATION: Synthetic Construct
```

-continued

```
<400> SEQUENCE: 22
gaaaactccc acagcaagct aatgattatc tgaattcatt caattgggag agacaagttt      60
cac                                                                   63

<210> SEQ ID NO 23
<211> LENGTH: 57
<212> TYPE: DNA
<213> ORGANISM: Artificial Sequence
<220> FEATURE:
<223> OTHER INFORMATION: Synthetic Construct

<400> SEQUENCE: 23
cacaagtgaa atatctggtt aggatagaat tctcccagtt ttcacaatga aaacatc        57

<210> SEQ ID NO 24
<211> LENGTH: 29
<212> TYPE: DNA
<213> ORGANISM: Artificial Sequence
<220> FEATURE:
<223> OTHER INFORMATION: Synthetic Construct

<400> SEQUENCE: 24
caagattgac aagagaaagg ggattgaag                                       29

<210> SEQ ID NO 25
<211> LENGTH: 63
<212> TYPE: DNA
<213> ORGANISM: Artificial Sequence
<220> FEATURE:
<223> OTHER INFORMATION: Synthetic Construct

<400> SEQUENCE: 25
ggaaaactcc cacagcaagc taatgattat ctgaattctc ccagttttca caatgaaaac     60
atc                                                                   63
```